United States Patent
Kornfield et al.

(10) Patent No.: US 10,427,995 B2
(45) Date of Patent: *Oct. 1, 2019

(54) MOLECULAR SIEVES MEDIATED UNSATURATED HYDROCARBON SEPARATION AND RELATED COMPOSITIONS, MATERIALS, METHODS AND SYSTEMS

(71) Applicant: CALIFORNIA INSTITUTE OF TECHNOLOGY, Pasadena, CA (US)

(72) Inventors: Julia A. Kornfield, Pasadena, CA (US); Mark E. Davis, Pasadena, CA (US); Ming-Hsin Wei, Pasadena, CA (US); Simon C. Jones, Whittier, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/146,019

(22) Filed: Sep. 28, 2018

(65) Prior Publication Data

US 2019/0100480 A1    Apr. 4, 2019

Related U.S. Application Data

(63) Continuation of application No. 15/391,795, filed on Dec. 27, 2016, now Pat. No. 10,112,878.

(60) Provisional application No. 62/387,373, filed on Dec. 24, 2015.

(51) Int. Cl.
| | | |
|---|---|---|
| *C07C 7/13* | (2006.01) | |
| *C08G 61/08* | (2006.01) | |
| *C08F 132/06* | (2006.01) | |

(52) U.S. Cl.
CPC ............... *C07C 7/13* (2013.01); *C08G 61/08* (2013.01); *C08G 2261/11* (2013.01); *C08G 2261/122* (2013.01); *C08G 2261/3322* (2013.01); *C08G 2261/3323* (2013.01); *C08G 2261/418* (2013.01)

(58) Field of Classification Search
CPC ........ C07C 7/13; C07C 13/263; C07C 13/267
USPC ............................ 526/75, 308; 585/803, 831
See application file for complete search history.

(56) References Cited

U.S. PATENT DOCUMENTS

| | | | | |
|---|---|---|---|---|
| 3,597,403 | A * | 8/1971 | Ofstead ................ | C08G 61/08 526/137 |
| 3,849,506 | A * | 11/1974 | Wilke .................... | C07C 2/02 560/1 |
| 10,112,878 | B2 * | 10/2018 | Kornfield .............. | C07C 7/13 |
| 2016/0067673 | A1 * | 3/2016 | Bats ...................... | B82Y 30/00 568/751 |
| 2017/0183277 | A1 | 6/2017 | Kornfield et al. | |

FOREIGN PATENT DOCUMENTS

WO    2017/112961 A1    6/2017

OTHER PUBLICATIONS

Marques, et al, "ZSM-5 acid zeolite supported metallocene catalysts for ethylene polymerization," Journal of Molecular Catalysis A: Chemical 192 (2003) 93-101. (Year: 2003).*
Baerlocher C, et al., "Atlas of Zeolites Framework Types" Sixth Edition Elsevier 2007 pp. 1-405.
International Preliminary Report on Patentability for International Application No. PCT/US2016/068766 filed on Dec. 27, 2016 on behalf of California Institute of Technology dated Jun. 26, 2018 9 pages.
Baerlocher C, et al., "Atlas of Zeolites Framework Types" Sixth Edition Elsevier 2007 pp. 1-405 (3 Parts).
Extended European Search Report for EP Application 16880170 filed on Dec. 27, 2016 on behalf of California Institute of Technology dated Jun. 24, 2019 7 pages.

* cited by examiner

*Primary Examiner* — Fred M Teskin
(74) *Attorney, Agent, or Firm* — Steinfl + Bruno, LLP

(57)    ABSTRACT

Described herein are compositions having an eight-membered monocyclic unsaturated hydrocarbon, methods and system to separate the eight-membered monocyclic unsaturated hydrocarbon at from a hydrocarbon mixture including additional nonlinear unsaturated $C_8H_2m$ hydrocarbons with $4 \leq m \leq 8$, by contacting the hydrocarbon mixture with a 10-ring pore molecular sieve having a sieving channel with a 10-ring sieving aperture with a minimum crystallographic free diameter greater than 3 Å and a ratio of the maximum crystallographic free diameter to the minimum crystallographic free diameter between 1 and 2, the molecular sieve having a T1/T2 ratio $\geq 20:1$ wherein T1 is an element independently selected from Si and Ge, and T2 is an element independently selected from Al, B and Ga, the 10-ring pore molecular sieve further having a counterion selected from $NH_4^+$, $Na^+$, $K^+$ and $Ca^{++}$.

32 Claims, 11 Drawing Sheets

| AlPO-11 | Type Material | AEL |

Crystal chemical data: [Al₂₀P₂₀O₈₀]-AEL
orthorhombic, Ibm2, a = 13.534Å, b = 18.482Å, c = 8.370Å
(Relationship to unit cell of Framework Type: a' = c, b' = b, c' = a )

Framework density: 19.1 T/1000Å³

Channels: [001] 10 4.0 x 6.5*

*10-ring viewed along [001]*

| Ferrierite | Type Material | FER |
|---|---|---|
Crystal chemical data: |Mg$^{2+}_2$Na$^+_2$ (H$_2$O)$_{18}$| [Al$_6$Si$_{30}$ O$_{72}$]-FER
orthorhombic, Immm, a = 19.156Å, b = 14.127Å, c = 7.489Å $^{(1)}$
Framework density: 17.8 T/1000Å$^3$
Channels: [001] 10 4.2 x 5.4* ↔ [010] 8 3.5 x 4.8*
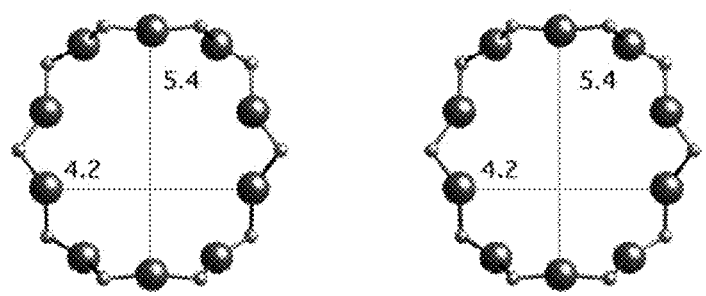
*10-ring viewed along [001]*
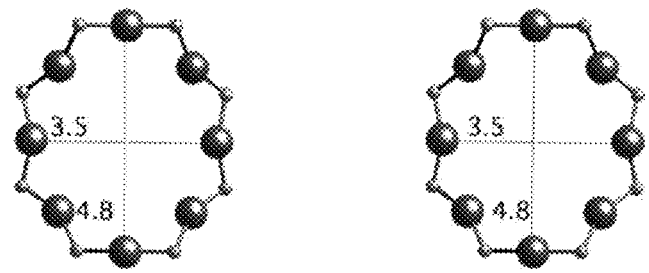
*8-ring viewed along [010]*
FIG. 3

10-Ring Structures

| Code | Name | Channels |
|---|---|---|
| AEL | AlPO-11 | {001} 10 4.0 x 6.5* |
| AFO | AlPO-41 | {001} 10 4.3 x 7.0* |
| AHT | AlPO-H2 | {001} 10 3.3 x 6.8* |
| CGF | Co-Ga-Phosphate-5 | {{100} 10 2.5 x 9.2* + 8 2.1 x 6.7*} ↔ [001] 8 2.4 x 4.8* |
| CGS | Co-Ga-Phosphate-6 | {[001] 10 3.5 x 8.1 ↔ [100] 8 2.5 x 4.6}*** |
| DAC | Dachiardite | [010] 10 3.4 x 5.3* ↔ [001] 8 3.7 x 4.8* |
| EUO | EU-1 | [100] 10 4.1 x 5.4* with large side pockets |
| FER | Ferrierite | [001] 10 4.2 x 5.4* ↔ [010] 8 3.5 x 4.8* |
| HEU | Heulandite | {[001] 10 3.1 x 7.5* ↔ 8 3.6 x 4.6*} ↔ [100] 8 2.8 x 4.7* |
| IMF | IM-5 | {[001] 10 5.5 x 5.6 ↔ [100] 10 5.3 x 5.4}** ↔ {[010] 10 5.3 x 5.9} ↔ {[001] 10 4.8 x 5.4 ↔ [100] 10 5.1 x 5.3}** |
| ITH | ITQ-13 | [001] 10 4.8 x 5.3* ↔ [010] 10 4.8 x 5.1* ↔ [100] 9 4.0 x 4.8* |
| LAU | Laumontite | [100] 10 4.0 x 5.3* (contracts upon dehydration) |
| MEL | ZSM-11 | <100> 10 5.3 x 5.4*** |
| MFI | ZSM-5 | {[100] 10 5.1 x 5.5 ↔ [010] 10 5.3 x 5.6}*** |
| MFS | ZSM-57 | [100] 10 5.1 x 5.4* ↔ [010] 8 3.3 x 4.8* |
| MTT | ZSM-23 | [001] 10 4.5 x 5.2* |
| MWW | MCM-22 | ⊥ [001] 10 4.0 x 5.5** ⊥ [001] 10 4.1 x 5.1** |
| NES | NU-87 | [100] 10 4.8 x 5.7** |
| OBW | OSB-2 | {<110> 10 5.0 x 5.0** ↔ {[001] 8 3.4 x 3.4* + <101> 8 2.8 x 4.0**} ↔ <100> 3.3 x 3.4**}*** |
| -PAR | Partheite | [001] 10 3.5 x 6.9* |
| PON | IST-1 | [100] 10 5.0 x 5.3* |
| RRO | RUB-41 | [100] 10 4.0 x 6.5* ↔ [001] 8 2.7 x 5.0* |
| SFF | SSZ-44 | [001] 10 5.4 x 5.7* |
| SFG | SSZ-58 | [001] 10 5.2 x 5.7* ↔ [100] 10 4.8 x 5.7* |
| STF | SSZ-35 | [001] 10 5.4 x 5.7* |
| STI | Stilbite | [100] 10 4.7 x 5.0* ↔ [001] 8 2.7 x 5.6* |
| SZR | SUZ-4 | {[001] 10 4.1 x 5.2 ↔ [010] 8 3.2 x 4.8 ↔ [110] 8 3.0 x 4.8}*** |
| TER | Terranovaite | [100] 10 5.0 x 5.0* ↔ [001] 10 4.1 x 7.0* |
| TON | Theta-1 | [001] 10 4.6 x 5.7* |
| TUN | TNU-9 | {[010] 10 5.6 x 5.5 ↔ [10$\bar{1}$] 10 5.4 x 5.5}*** |
| WEI | Weinebeneite | [001] 10 3.1 x 5.4* ↔ [100] 8 3.3 x 5.0* |
| -WEN | Wenkite | <100> 10 2.5 x 4.8** ↔ [001] 8 2.3 x 2.7* |

FIG. 9

MOLECULAR SIEVES MEDIATED UNSATURATED HYDROCARBON SEPARATION AND RELATED COMPOSITIONS, MATERIALS, METHODS AND SYSTEMS

CROSS REFERENCE TO RELATED APPLICATIONS

The present application is a continuation application of U.S. application Ser. No. 15/391,795 filed on Dec. 27, 2016 now U.S. Pat. No. 10,112,878 issued on Oct. 30, 2018, which claims priority to U.S. Provisional Application No. 62/387,373, entitled "Purification of Cyclic Olefins" filed on Dec. 24, 2015, the content of which is incorporated herein by reference in its entirety.

FIELD

The present disclosure relates to molecular sieves mediated unsaturated hydrocarbon separation and related compositions, materials, methods and systems.

BACKGROUND

Separations of chemical mixtures, inclusive of separation of a substance into its components as well as removal of impurities in a mixture comprising one or more components of interest, have been developed and are currently used in a large number of applications in fields such as medicine and manufacturing.

Separations differentiate among constituents in a mixture based on differences in chemical properties or physical properties such as size, shape, mass, density, or chemical affinity, between the constituents of a mixture. Separation processes are often classified according to the particular differences they use to achieve separation. If no single difference can be used to accomplish a desired separation, multiple operations will often be performed in combination to achieve a desired end.

Despite development of various methods, separation of mixtures of structurally similar components can still be challenging.

SUMMARY

Provided herein are molecular sieves mediated unsaturated hydrocarbon separation and related materials, compositions, methods and systems that in several embodiments allow separation of mixtures of unsaturated hydrocarbons having a similar molecular weight, molecular structure and/or polarity.

In particular, methods and systems and related materials and compositions that are based on the use of a 10-ring pore molecular sieve to separate an eight-membered monocyclic unsaturated hydrocarbon from a hydrocarbon mixture further comprising additional nonlinear unsaturated $C_8H_{2m}$ hydrocarbons with $4 \leq m \leq 8$, The 10-ring pore molecular sieve herein described has a sieving channel with a 10-ring sieving aperture with a minimum crystallographic free diameter greater than 3 Å and a maximum crystallographic free diameter to minimum crystallographic free diameter ratio between 1 and 2. The 10-ring pore molecular sieve herein described has a T1/T2 ratio≥20:1 wherein T1 is an element independently selected from Si and Ge or a combination thereof, and T2 is an element independently selected from Al, B and Ga or a combination thereof. The 10-ring pore molecular sieve herein described has a counterion selected from $NH_4^+$, $Na^+$, $K^+$ and $Ca^{++}$ or a combination thereof.

According to a first aspect, a method to separate an eight-membered monocyclic unsaturated hydrocarbon at an initial concentration $C_i$, from a hydrocarbon mixture further comprising additional nonlinear unsaturated $C_8H_{2m}$ hydrocarbons with $4 \leq m \leq 8$, the method comprising providing a 10-ring pore molecular sieve herein described having a sieving channel with a 10-ring sieving aperture with a minimum crystallographic free diameter greater than 3 Å and a ratio of the maximum crystallographic free diameter to the minimum crystallographic free diameter between 1 and 2. In the method the molecular sieve has a T1/T2 ratio≥20:1 wherein T1 is an element independently selected from Si and Ge or a combination thereof, and T2 is an element independently selected from Al, B and Ga or a combination thereof. In the method the 10-ring pore molecular sieve further having a counterion selected from $NH_4^+$, $Na^+$, $K^+$ and $Ca^{++}$ or a combination thereof. The method further comprises contacting the hydrocarbon mixture with the 10-ring pore molecular sieve at a temperature of −20° C. to 60° C. for a time and under conditions to obtain a sieved hydrocarbon mixture comprising the eight-membered monocyclic unsaturated hydrocarbon at a separation concentration $C_s > C_i$.

According to a second aspect, a sieved hydrocarbon mixture is described that is obtainable by separating an eight-membered monocyclic unsaturated hydrocarbon from a hydrocarbon mixture further comprising additional nonlinear unsaturated $C_8H_{2m}$ hydrocarbons with $4 \leq m \leq 8$, with methods herein described.

According to a third aspect, a method is described to provide an eight-membered monocyclic unsaturated hydrocarbon starting from precursors of the an eight-membered monocyclic unsaturated hydrocarbon, the method comprising reacting the precursors to provide the eight-membered simple-ring cyclic olefinic hydrocarbon in a hydrocarbon mixture comprising $C_8H_{2m}$ nonlinear olefinic hydrocarbons with $4 \leq m \leq 8$. The method further comprises contacting the hydrocarbon mixture with a 10-ring pore molecular sieve herein the described. In the method, the 10-ring pore molecular sieve has a sieving channel with a 10-ring sieving aperture with a minimum crystallographic free diameter greater than 3 Å and a ratio of the maximum crystallographic free diameter to the minimum crystallographic free diameter between 1 and 2 In the method, the 10-ring pore molecular sieve has a T1/T2 ratio≥20:1 wherein T1 is an element independently selected from Si, and Ge or a combination thereof, and T2 is an element independently selected from Al, B, and Ga or a combination thereof. In the method, the 10-ring pore molecular sieve has the 10-ring pore molecular sieve further having a counterion selected from $NH_4^+$, $Na^+$, $K^+$ and $Ca^{++}$ or a combination thereof. In the method, the contacting performed at a temperature of −20° C. to 60° C. for a time and under conditions to provide a sieved hydrocarbon mixture comprising the eight-membered monocyclic unsaturated hydrocarbon at a separation concentration $C_s \geq 99.3\%$ wt.

According to a fourth aspect, a system is described to provide an eight-membered monocyclic unsaturated hydrocarbon starting from precursors the eight-membered monocyclic unsaturated hydrocarbon, the system comprising one or more precursor of the eight-membered monocyclic unsaturated hydrocarbon; and a 10-ring pore molecular sieve herein the described. In the system, the 10-ring pore molecular sieve has a sieving channel with a 10-ring sieving aperture with a minimum crystallographic free diameter greater than 3 Å and a ratio of the maximum crystallographic free diameter to the minimum crystallographic free diameter between 1 and 2. In the system, the 10-ring pore molecular sieve has a T1/T2 ratio≥20:1 wherein T1 is an element independently selected from Si, Ge or a combination thereof, and T2 is an element independently selected from Al, B, and Ga or a combination thereof. In the system, the 10-ring pore molecular sieve has a counterion selected from $NH_4^+$, $Li^+$, $Na^+$, $K^+$ and $Ca^{++}$ or a combination thereof. In the system, the one or more precursors and the 10-ring pore molecular sieve are comprised for sequential use in the method to provide an eight-membered monocyclic unsaturated hydrocarbon herein described.

According to a fifth aspect, a hydrocarbon mixture comprising an eight-membered monocyclic unsaturated hydrocarbon and additional nonlinear unsaturated $C_8H_{2m}$ hydrocarbons with 4≤m≤8, the eight-membered monocyclic unsaturated hydrocarbon comprised in the hydrocarbon mixture at a concentration of at least 99.3% wt, or at least 99.5% wt, at least 99.7% wt, at least 99.8% wt, at least 99.9% wt or at least 99.99%.

According to a sixth aspect, a method is described to provide a hydrocarbon polymer starting from a hydrocarbon mixture comprising an eight-membered monocyclic unsaturated hydrocarbon and additional nonlinear unsaturated $C_8H_{2m}$ hydrocarbons with 4≤m≤8, the method comprising contacting the hydrocarbon mixture with a 10-ring pore molecular sieve herein described. In the method, the 10-ring pore molecular sieve has a sieving channel with a 10-ring sieving aperture with a minimum crystallographic free diameter greater than 3 Å and a ratio of the maximum crystallographic free diameter to the minimum crystallographic free diameter between 1 and 2. In the method, the 10-ring pore molecular sieve has a T1/T2 ratio≥20:1 wherein T1 is an element independently selected from Si, and Ge or a combination thereof, and T2 is an element independently selected from Al, B, and Ga or a combination thereof. In the method, the 10-ring pore molecular sieve has a counterion selected from $NH_4^+$, $Li^+$, $Na^+$, $K^+$ and $Ca^{++}$ or a combination thereof. In the method contacting the hydrocarbon mixture with a 10-ring pore molecular sieve is performed at a temperature of −20° C. to 60° C. for a time and under conditions to provide a sieved hydrocarbon mixture comprising the eight-membered monocyclic unsaturated hydrocarbon at a separation concentration $C_s$≥99.3% wt. The method further comprises contacting the sieved hydrocarbon mixture with a polymerization catalyst for a time and under condition to allow the eight-membered monocyclic unsaturated hydrocarbon to polymerize thus forming the hydrocarbon polymer.

According to a seventh aspect, a system is described to provide a polymer starting from a hydrocarbon mixture comprising an eight-membered monocyclic unsaturated hydrocarbon and additional nonlinear unsaturated $C_8H_{2m}$ hydrocarbons with 4≤m≤8, the system comprising a 10-ring pore molecular sieve and a polymerization catalyst. In the system the 10-ring pore molecular sieve has a sieving channel with a 10-ring sieving aperture with a minimum crystallographic free diameter greater than 3 Å and a ratio of the maximum crystallographic free diameter to the minimum crystallographic free diameter between 1 and 2. In the system the 10-ring pore molecular sieve has a T1/T2 ratio≥20:1 wherein T1 is an element independently selected from Si, and Ge or a combination thereof, and T2 is an element independently selected from Al, B, and Ga or a combination thereof. In the system the 10-ring pore molecular sieve has a counterion selected from $NH_4^+$, $Na^+$, $K^+$ and $Ca^{++}$ or a combination thereof. In the system the 10-ring pore molecular sieve and the polymerization catalyst are comprised for sequential use in the method to provide a polymer comprising at least one eight-membered cyclic hydrocarbon ring monomer starting from hydrocarbon mixture herein described.

According to an eighth aspect, a method is described to provide a hydrocarbon polymer starting from precursors of an eight-membered monocyclic unsaturated hydrocarbon, the method comprising reacting the precursors to provide the an eight-membered monocyclic unsaturated hydrocarbon in a hydrocarbon mixture further comprising additional nonlinear unsaturated $C_8H_{2m}$ hydrocarbons with 4≤m≤8. The method further comprises contacting the hydrocarbon mixture with a 10-ring pore molecular sieve herein described. In the method, the 10-ring pore molecular sieve has a sieving channel with a 10-ring sieving aperture with a minimum crystallographic free diameter greater than 3 Å and a maximum crystallographic free diameter to minimum crystallographic free diameter ratio between 1 and 2. In the method, the 10-ring pore molecular sieve has a T1/T2 ratio≥20:1 wherein T1 is an element independently selected from Si, and Ge or a combination thereof, and T2 is an element independently selected from Al, B, and Ga or a combination thereof. In the method, the 10-ring pore molecular sieve has a counterion selected from $NH_4^+$, $Na^+$, $K^+$ and $Ca^{++}$ or a combination thereof. In the method, contacting the hydrocarbon mixture with a 10-ring pore molecular sieve is performed at a temperature of −20° C. to 60° C. for a time and under conditions to provide a sieved hydrocarbon mixture comprising the an eight-membered monocyclic unsaturated hydrocarbon at a separation concentration $C_s$≥99.3% wt. The method further comprises contacting the sieved hydrocarbon mixture with a polymerization catalyst for a time and under condition to allow the eight-membered monocyclic unsaturated hydrocarbon to polymerize thus forming the hydrocarbon polymer.

According to a ninth aspect, a system is described to provide a polymer starting from precursors of an eight-membered monocyclic unsaturated hydrocarbon, the system comprising one or more precursors of an eight-membered monocyclic unsaturated hydrocarbon, a 10-ring pore molecular sieve and a polymerization catalyst. In the system, the 10-ring pore molecular sieve has a sieving channel with a 10-ring sieving aperture with a minimum crystallographic free diameter greater than 3 Å and a ratio of the maximum crystallographic free diameter to the minimum crystallographic free diameter between 1 and. In the system, the 10-ring pore molecular sieve has a T1/T2 ratio≥20:1 wherein T1 is an element independently selected from Si, and Ge or a combination thereof, and T2 is an element independently selected from Al, B, and Ga or a combination thereof. In the system, the 10-ring pore molecular sieve has a counterion selected from $NH_4^+$, $Na^+$, $K^+$ and $Ca^{++}$ or a combination thereof. In the system, the one or more precursors of an eight-membered monocyclic unsaturated hydrocarbon, the 10-ring pore molecular sieve and the polymerization catalyst for sequential use in the method to provide a polymer starting from precursors of an eight-membered cyclic hydrocarbon ring monomer herein described.

The molecular sieves mediated olefin separation method and related materials, compositions and systems allow in some embodiments to separate cyclic olefins such as cyclooctene, cyclooctadiene, cyclooctatriene, cyclooctatetraene and cyclododecatriene with a higher purity and/or yield compared to purity and yields achievable with separation performed with conventional methods.

The molecular sieves mediated olefin separation herein described and related materials, compositions, methods and systems, allow in some embodiments to obtain highly-pure reagents or monomers that undergo useful reactions with high fidelity.

In particular, the molecular sieves mediated olefin separation herein described and related materials, compositions, methods and systems allow in some embodiments to obtain prepare highly-pure monomers that polymerize at extremely-low catalyst loadings to give controlled, high-molecular weight functionalized polymers with high fidelity.

The molecular sieves mediated olefin separation herein described and related materials, compositions, methods and systems allow in some embodiments to provide simple, cost-effective purification methods to remove impurities from cyclic olefin monomers such as cyclooctene, cyclooctadiene and cyclododecatriene.

The molecular sieves mediated olefin separation, herein described and related compositions, materials, methods, and systems can be used in several embodiments in connection with applications wherein separation of cyclic olefins with high purity is desirable, including but not limited to manufacturing of polymers, catalysts and other fine chemicals suitable to be used in applications such as fuels and more particularly crude oils and refined fuels, inks, paints, cutting fluids, drugs, lubricants, pesticides and herbicides as well adhesive processing aids, personal care products (e.g. massage oils or other non-aqueous compositions) and additional applications which are identifiable by a skilled person. Additional applications comprise industrial processes in which reduction of flow resistance, mist control, lubrication, and/or control of viscoelastic properties (for example, to improve the viscosity index of a non-polar composition) of a non-polar composition and in particular a liquid non-polar composition is desired.

The details of one or more embodiments of the disclosure are set forth in the accompanying drawings and the detailed description and examples below. Other features, objects, and advantages will be apparent from the detailed description, examples and drawings, and from the appended claims

BRIEF DESCRIPTION OF THE DRAWINGS

The accompanying drawings, which are incorporated into and constitute a part of this specification, illustrate one or more embodiments of the present disclosure and, together with the detailed description and the examples, serve to explain the principles and implementations of the disclosure.

FIG. 3 shows a schematic summary of the features of molecular sieve Ferrierite from Atlas of Zeolites Framework Types by Ch. Baerlocher W. M. Meier and D. H Olson, Sixth Edition Elsevier.

FIG. 9 shows a list of molecular sieves with related features from Atlas of Zeolites Framework Types by Ch. Baerlocher W. M. Meier and D. H Olson, Sixth Edition Elsevier.

DETAILED DESCRIPTION OF PREFERRED EMBODIMENTS

Figure 1:
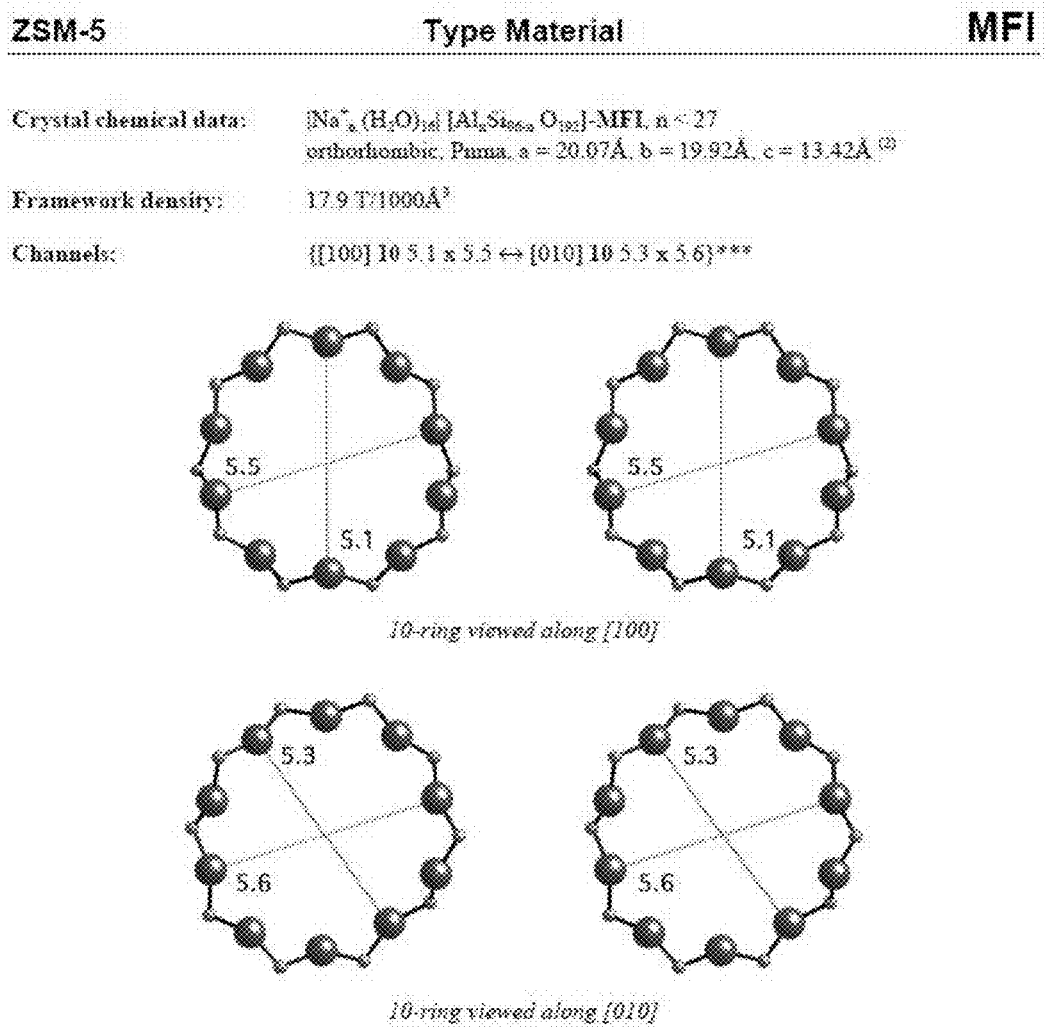
FIG. 1 shows a schematic summary of the features of the exemplary molecular sieve ZSM-5 from Atlas of Zeolites Framework Types by Ch. Baerlocher W. M. Meier and D. H Olson, Sixth Edition Elsevier.

Provided herein is a molecular sieve mediated olefin separation and related materials, compositions, methods and systems that in several embodiments allow separation of mixtures of cyclic olefins having a similar molecular weight and molecular structure.

The term "molecular sieves" as used herein refers to a crystalline porous solid having interconnected channels of same or different sizes defined by rings of tetrahedra forming the crystalline structure of the solid. A tetrahedron is the basic building unit of a molecular sieve and each tetrahedron is formed by a central atom with relatively low electronegativity, e.g., Si(IV), Ge(IV) Al(III), B(III), Ga(III), P(V), and Zn(II) (also identified as T-atom) and oxygen anions occupying the corners of the tetrahedron. These combinations can be depicted as $[SiO_4]$, $[AlO_4]$, $[PO_4]$, etc.

In a molecular sieve, the tetrahedra formed by various combinations of T-atoms according to the material of the sieve, are linked via the apical oxygen (T-O-T) to form rings of tetrahedra of different sizes. In general, a ring containing n tetrahedral T-atoms is called an "n-ring." The most common n-rings contain 4, 5, 6, 8, 10, or 12 tetrahedra, but materials with rings formed of 14, 18, up to 20 tetrahedra have been prepared. Materials with 3-, 7- or 9-rings, are rare as will be understood by a skilled person.

In a molecular sieve, the n-rings form part of the crystalline structure of the molecular sieve also indicated as crystalline framework of the molecular sieves. Crystalline frameworks can be grouped according to "framework types" as would be understood by a skilled person. The term "framework type", as used herein with reference to of a molecular sieve having a framework formed by one or more T-atoms indicates the idealized structure of the framework provided by replacing the T-atoms of the framework with Si T-atoms only. Accordingly, an unlimited number molecular sieves with different T-atoms and different compositions can and do have a same framework type as will be understood by a skilled person. The structure commission of the International Zeolite Association (IZA) periodically reviews publications containing new tetrahedral frameworks and assigns a "three-letter code" to each distinct new framework type (see e.g. SZR, MTT, TON, MWW, MFI, ETL, FER, MEL, EUO, LAU and others identifiable by a skilled person). At the filing date of the present disclosure, there are at least 176 different framework types with assigned three-letter codes. Description of a specific molecular sieve typically includes the framework type and the selection of T-atoms as will be understood by a skilled person.

In a molecular sieve, the n-rings forming part of the crystalline framework) define cavities, channels and other structures such as chains and cages, as will be understood by a skilled person.

The term "cavity" as used herein refers to a polyhedral enclosure formed by n-rings with the largest of the n-rings forming the enclosure defining an opening (herein also "aperture") which allows the passage of molecules larger than water to move in and out of the polyhedral enclosure. Accordingly, an "aperture" as used herein indicate an opening of a cavity which allows the passage of molecules larger than water to move in and out of the cavity. In a molecular sieve, cavities can be connected one to another to form "channels".

The term "channel" as used herein refers to a plurality of connected cavities infinitely extended in at least one dimension. The "minimum aperture" of a channel refers to the smallest aperture of the channel. The "pore" of a channel refers to the crystallographic cross section through which a molecule can pass at the minimum aperture of a channel.

In a molecular sieve, the minimum aperture of a channel limits the size of molecules that can diffuse along the channel. In a sieve, the channel having the largest minimum aperture compared to the other channels of the sieve, is herein also called "sieving channel". A sieving channel of a particular molecular sieve has a minimum aperture herein also indicated as "sieving aperture" which defines the minimum dimension of the compounds that can be sieved with that particular molecular sieve. Additional channels can be comprised in the molecular sieves that interconnect with one or more sieving channels. Those additional channels can be sieving channels and/or "venting channels" which are channels other than a sieving channel that intersects with the sieving channel. Venting channels provide a path for small adsorbates to leave the sieving channel. In a molecular sieve, sieving channels and/or venting channels can be interconnected to form a 3D, or a 2D channel network. The existence, number and orientation of channels, including sieving channels, in a particular molecular sieve is determined by its framework type. The framework type specifies the number of T-atoms in the n-ring that encloses the minimum aperture of a channel in any molecular sieve having that framework type.

In a molecular sieve, channels and in particular sieving channels can be characterized by their crystallographic diameter. The "crystallographic diameter" of a channel as used herein indicates the crystallographic distance between centers of oxygen atoms at opposite sides of the n-ring that forms the minimum aperture of a channel. The "crystallographic free diameter" of a channel as used herein is 2.7 Å less than the crystallographic diameter of the channel. This value is chosen based on the ionic radius of oxygen, which is approximately 1.35 Å. In general, the minimum aperture of a channel is not circular. Therefore, a channel is usually characterized by two crystallographic free diameters, and in particular by the diameter defined by the smallest crystallographic distance between centers of oxygen atoms at opposite sides of the n-ring that forms the minimum aperture of a channel (minimum crystallographic free diameter) and the diameter defined by the largest crystallographic distance between centers of oxygen atoms at opposite sides of the n-ring that forms the minimum aperture of a channel (maximum crystallographic free diameter). The values of minimum and maximum crystallographic diameters are identifiable by a skilled person. In particular, the minimum and maximum crystallographic free diameters of the sieving channel for each specific framework type is tabulated by the Structure Commission of the International Zeolite Association and described for example in the periodical publication Atlas of Zeolites Framework Types, Published regularly by Elsevier. The Sixth Edition of Atlas of Zeolites Framework Types by Ch. Baerlocher W. M. Meier and D. H Olson in particular is incorporated herein by reference in its entirety.

Molecular sieves can be categorized based on the minimum aperture of their respective sieving channel. Accordingly, a molecular sieve in which the sieving channel has minimum aperture defined by a 8-ring is identified as an "8-ring molecular sieve" or a "small-pore molecular sieve," and a molecular sieve in which the sieving channel has a minimum aperture defined by a 10-ring is identified as a "10-ring molecular sieves" or a "medium-pore molecular sieve," and a molecular sieve in which the sieving channel has a minimum aperture defined by a 12-ring is identified as a "12-ring molecular sieve" or "large-pore molecular sieve." The precise size and shape of the pore of a specific channel in a specific molecular sieve depends on the framework type, selection of T-atoms, counter ion and temperature. Nevertheless, the typical values of the free diameters show an increasing trend with increasing numbers of tetrahedra encircling the largest pore of a channel with "small-pore," "medium-pore" and "large-pore" zeolites having free diameters of approximately 4.0 Å, 5.6 Å and 7.6 Å, respectively.

Figure 2:
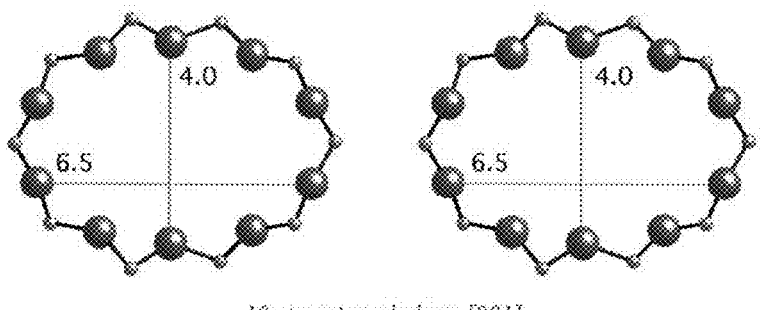
FIG. 2 shows a schematic summary of the features of the exemplary molecular sieve Apo-11 from Atlas of Zeolites Framework Types by Ch. Baerlocher W. M. Meier and D. H Olson, Sixth Edition Elsevier.

A schematic of exemplary 10-ring molecular sieves from Atlas of Zeolites Framework Types by Ch. Baerlocher W. M. Meier and D. H Olson sixth edition inclusive of information concerning their respective minimum and maximum crystallographic free diameters are reported with the respective framework type in FIGS. 1 to 3.

Molecular sieves in the sense of the disclosure can also be categorized based on the ratios of the elements which form the T-atoms of the tetrahedra in view of the actual material forming the molecular sieve. Several molecular sieves comprise two T-atoms selected among trivalent, tetravalent or pentavalent elements and the related structure can be characterized by the related ratio as will be understood by a skilled person. For example, molecular sieves in the sense of the disclosure comprise crystalline metal aluminosilicates having a three-dimensional interconnecting network of silica and alumina tetrahedrals presenting oxygens on their apices, also indicated as zeolites as well as additional sieves such as borosilicates, gallogermanates, and many other materials that have an open three-dimensional network of 4-connected tetrahedra. Zeolites, borosilicates, and gallogermanates can be characterized by the respective Si/Al, Si/B and Ge/Ga ratios as will be understood by a skilled person.

Molecular sieves in the sense of the disclosure can comprise one or more cations also indicated as "counterions" to neutralize negative charges introduced by having tetrahedrals formed by trivalent rather than tetravalent T-atoms. Common counterions include sodium ion ($Na^+$), potassium ion ($K^+$), ammonium ion ($NH_4^+$), calcium ion ($Ca^{++}$), and proton ($H^+$). Selection of a proper counterion in a zeolite framework can be achieved, as understood by a skilled person in the art, by using an aqueous mineralizing medium with the desired cation in the hydrothermal synthesis of a zeolite or by subsequent ion exchange (see Cundy and Cox, *Microporous and Mesoporous Materials,* 2005, 82(1-2), 1-78). Typically molecular sieves are synthesized by combining non-molecular building blocks such as alumina and silica with a chosen alkali metal hydroxide and water, then incubating the mixture in the presence of organic chemicals called Structure Directing Agents (SDAs) in an enclosed environment at an appropriate temperature in the range 50-200° C. for an appropriate period of time. The SDA is selected such that it influences the self-assembly of the molecular sieve toward a desired framework type. The final structure is a product of synthetic conditions and post-synthetic treatment, including the conditions used to decompose and remove the SDA and subsequent ion exchange to introduce a desired counterion.

Molecular sieves in the sense of the disclosure can also comprise water and the molecular sieves can also have a water content referred to as the weight fraction of water bound to the interior of a zeolite (such as cavities and channels) by interactions of physical nature in a zeolite (see Esposito et al., *Microporous and Mesoporous Materials,* 2015, 202, 36-43). The water content of a zeolite can be experimentally determined by measuring the weight loss of a zeolite sample due to heating to elevated temperature (such as 600° C.) under inert atmosphere using thermal gravimetric analysis (TGA) and additional methods as will be understood by a skilled person. The ratio of trivalent T-atoms to tetravalent T-atoms correlates with the number of negatively charged sites on the inorganic crystal framework. Increasing the number of charges sites on the framework tends to increase the amount of water absorbed by a molecular sieve and tends to increase the difficulty of driving water out of the pores to make them available for sieving the hydrocarbon molecules of the present invention.

Molecular sieves in the sense of the disclosure can be used in methods and systems herein described to perform separation of an eight-membered monocyclic ring unsaturated hydrocarbon from a mixture of unsaturated hydrocarbons as will be understood by a skilled person.

The word "separation" as used herein indicates a process directed to convert a mixture of chemical substances into two or more distinct product mixtures, at least one of which is enriched in one or more of the mixture's constituents. In particular, the word separation as used herein indicates a process that removes, isolates, separates, enriches or depletes one or more substances from a mixture by methods that involve differences in the chemical or physical properties of the substances involved, such as extraction, distillation, selective sieving, and selective chemical consumption of undesired components. The goals of performing a separation process include increasing concentrations of desired components in a mixture and reducing concentrations of undesired components that can interfere with an intended application of the desired component or components in a mixture. While distillation is the most commonly used method to separate hydrocarbons with different boiling points, selective adsorption by ordered porous materials such as a molecular sieve is known to a skilled person in the art as an effective method to separate hydrocarbon molecules that have similar molecular weights and boiling points yet different size or shape. A skilled person in the art can understand that selective reaction can also be used to separate hydrocarbon isomers with same molecular weight and difference in boiling points≤30° C. (which is too low to allow efficient separation using distillation). Approaches to overcome this difficulty by preferentially consuming the undesired component or components using a chemical reaction are exemplified in Ji et al., *Macromolecules* 2004, 37, 5485-5489: the fact that terminal double bonds (also known as vinyl groups) react faster with borane-tetrahydrofuran ($BH_3.THF$) than non-terminal double bonds by a factor of 14 was used to remove 4-vinyl-1-cyclohexene (VCH), which is an isomer of cis,cis-1,5-cyclooctadiene (COD) present in the commercially available COD at 0.2-0.5 wt % and has a boiling point 20° C. lower than that of COD, from COD with a 40% loss of COD in the process.

The wording unsaturated hydrocarbons as used herein indicates hydrocarbons that have double or triple covalent bonds between adjacent carbon atoms. In particular unsaturated hydrocarbons with at least one carbon-to-carbon double bond are called alkenes or olefins and those with at least one carbon-to-carbon triple bond are called alkynes. The word "olefin" as used herein indicates a compound also called alkene, formed by hydrogen and carbon and containing one or more pairs of carbon atoms linked by a double bond. Unsaturated hydrocarbons are more reactive than alkanes due to the reactivity of the carbon-carbon double bond or carbon-carbon triple bond and the presence of allylic C—H centers. Unsaturated hydrocarbons can be classified based on the number of double bonds or triple bonds in the compounds (see e.g. monoolefins or monoalkyne, diolefins or dialkynes, triolefins trialkynes, etc., in which the number of double bonds or triple bonds per molecule is, respectively, one, two, three, or some other number). Olefins can also be classified based on cys-trans-isomerism of H or C atoms with respect to at least one non-terminal double bond given that fact that a double bond cannot rotate: if the two hydrogen atoms attached to a carbon-carbon double bond are on the same side of the said double bond, the isomer is a cis olefin; if the two hydrogen atoms lie on opposite side of the double bond, the isomer is a trans olefin.

Unsaturated hydrocarbons can also be classified as cyclic or acyclic unsaturated hydrocarbons, in which the double bond is located between carbon atoms forming part of a cyclic (closed-ring) or of an acyclic (open-chain) grouping, respectively. In particular, the wording "cyclic unsaturated hydrocarbons" as used herein indicates a type of alkene or alkyne hydrocarbon which is both aliphatic and cyclic, having at least one closed unsaturated ring of carbon atoms but do not have aromatic character. The term "monocyclic unsaturated hydrocarbon" or "monocyclic unsaturated hydrocarbon" as used herein refers to cyclic unsaturated hydrocarbons where the carbon atoms forming part of a cyclic grouping are within a single closed ring which has one or more pairs of carbon atoms linked by a double bond or triple bond. Examples of monocyclic cycloalkenes are cyclopropene, cyclobutene, cyclopentene, cyclopentadiene, cyclohexene, cyclohexadiene, cycloheptene, cycloheptadiene, cyclooctene, cyclooctadiene. Some cycloalkenes, such as cyclobutene, cyclopentene and cyclooctadiene can be used as monomers to produce polymer chains. Due to geometrical considerations, smaller cycloalkenes are typically cis isomers, even if the term cis tends to be omitted from the names. In larger rings (from around 8 atoms), cis-trans isomerism of the double bond can occur.

The term "bicyclic unsaturated hydrocarbon" as used herein refers to hydrocarbon compounds in which the carbon atoms forming part of a cyclic grouping are contained in two rings having at least one common carbon atom, and at least one pair of carbon atoms in at least one of the two rings is linked by a double bond or a triple bond. Structures that have two rings that share one or more carbon atoms may be designated by specialized names: "spiro" if the two rings share one carbon atom, "fused" if the two rings share two adjacent carbon atoms, and "bicycle" if the two rings share non-adjacent carbon atoms. Examples of $C_8H_{12}$ bicyclic olefins are bicyclo[3.3.0]oct-2-ene and bicyclo[3.2.1]oct-2-ene.

Cyclic unsaturated hydrocarbon can be categorized based on the total number of carbon atoms in the compound which is indicated. In particular, cyclic or acylic unsaturated carbons have $C_nH_{2(n-k-j+1)}$ wherein n is the total number of C atoms in the unsaturated carbon atoms, k is the degree of unsaturation (1 for a double bond, 2 for a triple bond) in the olefins and j is the number of rings in the unsaturated hydrocarbon. Cyclic unsaturated hydrocarbons can be categorized based on the number of carbon atoms in each of the one or more closed rings of carbon atoms. For example, unsaturated monocyclic hydrocarbons can be can be categorized in 10-membered monocyclic unsaturated hydrocarbons, 9-membered monocyclic unsaturated hydrocarbons 8-membered monocyclic unsaturated hydrocarbons, 6-membered monocyclic unsaturated hydrocarbons and so on, based on the number of carbon atoms forming the single ring of the monocyclic unsaturated hydrocarbon.

Unsaturated hydrocarbons, and in particular cyclic olefins, that have a same total number of carbon atoms and a same number of rings have structure, molecular weight and polarity that are very similar (within a 5% range) which makes the related separation particularly challenging. In particular eight-membered monocyclic unsaturated hydrocarbon can be challenging to separate from mixtures further including other unsaturated monocyclic hydrocarbons having the same total number carbon atoms.

In embodiments herein described, a method is described to separate eight-membered monocyclic unsaturated hydrocarbon from a hydrocarbon mixture comprising further comprising additional nonlinear unsaturated $C_8H_{2m}$ hydrocarbons with $4 \leq m \leq 8$.

A "hydrocarbon mixture" in the sense of the disclosure indicates a composition comprising hydrocarbons with various number of carbon atoms and degree of saturation. Hydrocarbons that can be part of a hydrocarbon mixture comprise linear branched or cyclic, alkane, alkene, alkyne as well as aromatic hydrocarbon as will be understood by a skilled person. A hydrocarbon mixture can be solid, liquid or gaseous depending on the composition of the mixture.

In embodiments herein describe a hydrocarbon mixture comprises $C_8H_{2m}$ hydrocarbons with $4 \leq m \leq 8$, wherein m=n-k-j+1, which comprises non-linear unsaturated hydrocarbons having a total of C atoms n=8. Non-linear unsaturated hydrocarbons of the $C_8H_{2m}$ hydrocarbons comprise in particular, cyclic unsaturated hydrocarbons and unsaturated hydrocarbons with at least one branch, and possibly two, or four branches. In the hydrocarbon mixture, one of the $C_8H_{2m}$ hydrocarbons is an eight-membered monocyclic unsaturated hydrocarbon and in particular an eight-membered monocyclic olefin.

In particular, methods and systems herein embodiments herein described are directed to separate the eight-membered monocyclic unsaturated hydrocarbon from the hydrocarbon mixture further comprising additional nonlinear unsaturated $C_8H_{2m}$ hydrocarbons with $4 \leq m \leq 8$.

In particular, in some embodiments, the eight-membered monocyclic unsaturated hydrocarbon can have one, two, three, or four double bonds or one or two triple bonds. In particular, in some embodiments, one or more of the 8-membered monocyclic unsaturated hydrocarbons can be any one of compounds 1-10.

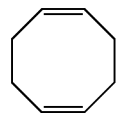

1

2

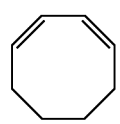

3

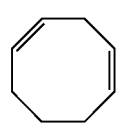

4

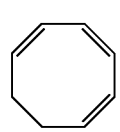

5

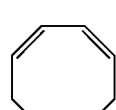

6

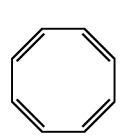

7

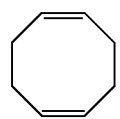

8

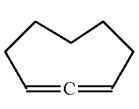

9

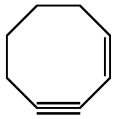

10

In some embodiments, the hydrocarbon mixture comprises one or more eight membered monocyclic unsaturated hydrocarbons in various combinations. The total concentration of the one or more eight membered monocyclic unsaturated hydrocarbons in a hydrocarbon mixture to be subjected to separation is herein indicated as $C_i$ which is the initial concentration of eight membered monocyclic unsaturated hydrocarbons and can be typically expressed in terms of weight percent or mole percent.

In methods herein described the method is directed to separate eight-membered monocyclic unsaturated hydrocarbon from a hydrocarbon mixture further comprising additional nonlinear unsaturated $C_8H_{2m}$ hydrocarbons with $4 \leq m \leq 8$, which can comprise three-membered, four-membered five-membered and six-membered monocyclic or bicyclic unsaturated hydrocarbons and in particular, three-membered, four-membered five-membered and six-membered monocyclic or bicyclic olefins.

In some embodiments, the three-membered to six-membered cyclic olefins can have formula (I)

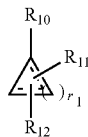

Formula (I)

wherein

------ represents a single bond, or a double bond;
r1 represents 1 to 4;
R10, R11 and R12 are independently selected from H, C1 to C5 linear, branched or cyclic alkyl, alkenyl, or an alkynyl groups, wherein the R11 and R12 are on a same carbon or a different carbon of a ring, and wherein R10, R11 and R12 together contain (6-r1) carbon atoms.

In some embodiments, Formula (I) has a chemical formula of $C_8H_{12}$, wherein r1 is 4, the Formula (I) includes the Formula (I)(6a) to Formulas (I)(6a) to (I)(6k)

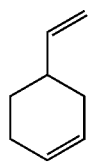
(I)(6a)

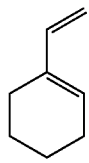
(I)(6b)

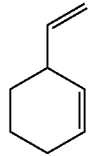
(I)(6c)

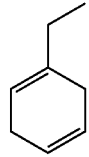
(I)(6d)

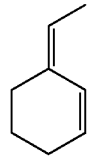
(I)(6e)

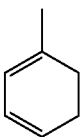
(I)(6f)

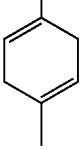
(I)(6g)

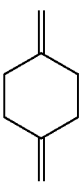
(I)(6h)

(I)(6i)

(I)(6j)

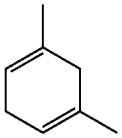
(I)(6k)

In some embodiments, Formula (I) has a chemical formula of $C_8H_{12}$, and wherein r1 is 3, the Formula (I) includes the Formula (I)(5a) to Formulas (I)(a) to (I)(5f)

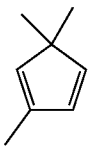
(I)(5a)

(I)(5b)

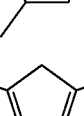
(I)(5c)

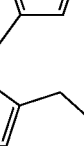
(I)(5d)

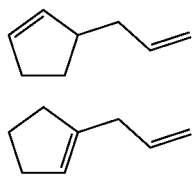
(I)(5e)

(I)(5f)

In some embodiments, Formula (I) has a chemical formula of $C_8H_{12}$, and wherein r1 is 2, the Formula (I) includes the Formula (I)(4a) to Formulas (I)(a) to (I)(4g)

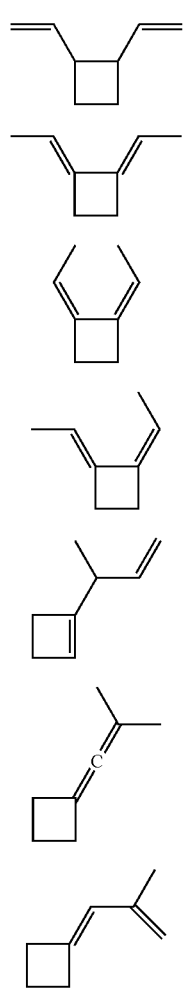

(I)(4a)

(I)(4b)

(I)(4c)

(I)(4d)

(I)(4e)

(I)(4f)

(I)(4g)

In some embodiments, Formula (I) has a chemical formula of C8H10, and wherein r1 is 4, the Formula (I) includes the Formula (I)(6l) to Formulas (I)(6t)

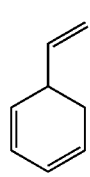
(I)(6l)

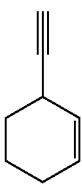

(I)(6m)

(I)(6n)

(I)(6o)

(I)(6p)

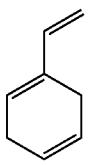

(I)(6q)

(I)(6r)

(I)(6s)

(I)(6t)

In some embodiments, Formula (I) has a chemical formula of C8H10, and wherein r1 is 3, the Formula (I) includes the Formula (I)(5g) to Formulas (I)(5j)

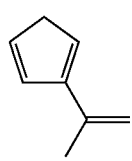
(I)(5g)

-continued (I)(5h)

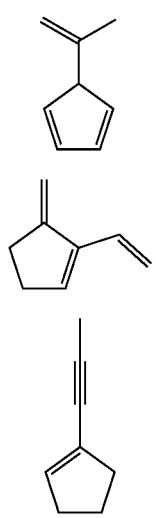

(I)(5i)

(I)(5j)

In some embodiments, Formula (I) has a chemical formula of C8H10, and wherein r1 is 1, the Formula (I) includes the Formula (I)(3a) to Formulas (I)(3b)

(I)(3a)

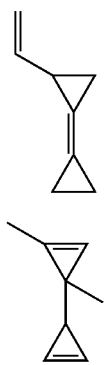

(I)(3b)

In some embodiments, the three-membered to six-membered cyclic olefins of a hydrocarbon mixture herein described have formula (II)

Formula (II)

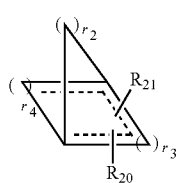

wherein
------ represents a single bond, or a double bond;
r2, r3 and r4 each represents 0 to 4, wherein r2, r3 and r4 together is 2 to 6, and r2+r3, r3+r4 and r2+r4 are 0 to 4;
R20, R21 are independently selected from H, C1 to $C_4$ linear, branched or cyclic alkyl, alkenyl, alkynyl, groups, wherein the R20 and R21 are on a same or a different carbon of a ring and wherein R20 and R21 together contain (6-r2-r3-r4) carbon atoms.

In some embodiments, the three-membered to six-membered cyclic olefins of Formula (II) can have chemical formula of $C_8H_{12}$, and in some of these embodiments when r2 equals to 0, the Formula (II) can include the Formula (II)(a) to Formulas (II)(d)

(II)(a)

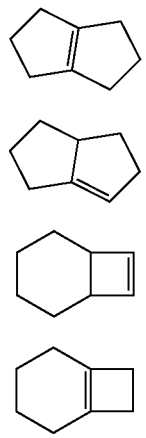

(II)(b)

(II)(c)

(II)(d)

In some embodiments, the three-membered to six-membered cyclic olefins of Formula (II) can have chemical formula of $C_8H_{12}$, and Formula (II) and in some of these embodiments when r2 is 1, the Formula (II) can include the Formula (II)(e) to Formulas (II)(g)

(II)(e)

(II)(f)

(II)(g)

In some embodiments, the three-membered to six-membered cyclic olefins of Formula (II) can have chemical formula of $C_8H_{12}$, and in some of these embodiments when r2 is 2, the Formula (II) include Formula (II)(j)

(II)(j)

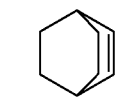

In some embodiments, the three-membered to six-membered cyclic olefins of Formula (II) can have chemical formula of $C_8H_{10}$, and in some of these embodiments when r2 is 0, Formula (II) can include the Formula (II)(k) to Formulas (II)(p)

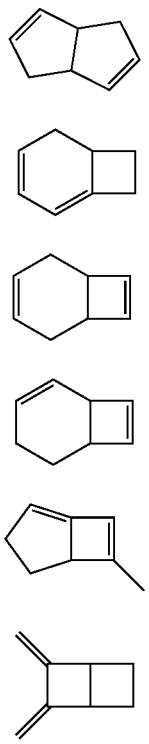

(II)(k)

(II)(l)

(II)(m)

(II)(n)

(II)(o)

(II)(p)

In some embodiments, the three-membered to six-membered cyclic olefins of Formula (II) can have chemical formula of $C_8H_{10}$, and in some of these embodiments when r2 is 1, the Formula (II) includes Formula (II)(s)

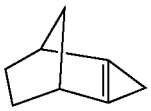

(II)(s)

In some embodiments, C8 acyclic olefins have formula (III)

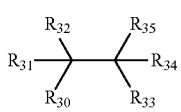

Formula (III)

wherein R30 to R35 are independently selected from H, C1 to C6 linear, branched alkyl, alkenyl, alkynyl, groups, wherein R30 to R35 represent separate groups or any two of R30 to R32 or R33 to R35 include at least one tertiary or quaternary carbon, wherein R30 to R35 together contains 6 carbons.

In some embodiments, the three-membered to six-membered cyclic olefins of Formula (III) can have chemical formula of $C_8H_{10}$, and can include compounds of Formula (III)(a) to Formulas (III)(f)

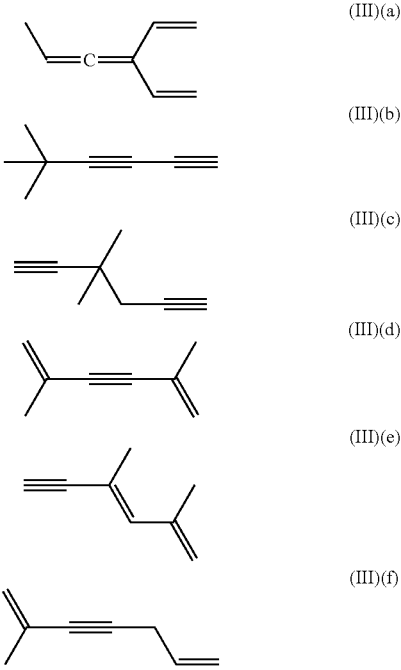

(III)(a)

(III)(b)

(III)(c)

(III)(d)

(III)(e)

(III)(f)

In some embodiments, the three-membered to six-membered cyclic olefins of Formula (III) $C_8H_{12}$, and can include compounds of Formula (III)(r) to Formulas (III)(v)

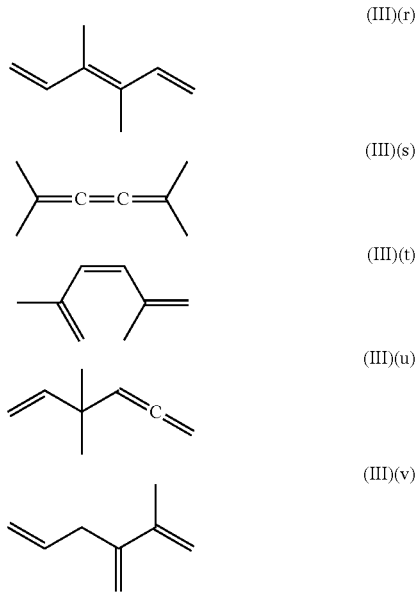

(III)(r)

(III)(s)

(III)(t)

(III)(u)

(III)(v)

In methods to separate nonlinear unsaturated hydrocarbon compounds are separated from the hydrocarbon, the hydrocarbon mixture is contacted with a 10-ring pore molecular sieve having a sieving channel with a 10-ring sieving aperture with a minimum crystallographic free diameter greater than 3 Å and a maximum crystallographic free diameter to minimum crystallographic free diameter ratio between 1 and 2.

In some embodiments, the 10-ring pore molecular sieve can have a minimum crystallographic free diameter of the sieving aperture of the sieving channel, equal to or higher than 4.0 Å, or equal to or higher than 4.5 Å, equal to or higher than 5 Å, or less than 6 Å.

In some embodiments, the 10-ring pore molecular sieve can have a maximum crystallographic free diameter to minimum crystallographic free diameter ratio of the sieving aperture between 1.1 and 1.20, or between 1.21 to 1.40, or between 1.41 to 1.80.

In some embodiments, the 10-ring pore molecular sieve can have a maximum crystallographic free diameter to minimum crystallographic free diameter ratio of the sieving aperture of 1.1, or 1.25, or 1.5.

In some embodiments, the 10-ring pore molecular sieve can have a minimum crystallographic free diameter of the sieving aperture is equal to or greater than 4.0 Å to less than 4.5 Å and a maximum crystallographic free diameter to minimum crystallographic free diameter ratio of the sieving aperture of 1.25 to 1.5 (herein 10-ring pore narrow molecular sieve).

In some embodiments, the 10-ring pore molecular sieve can have a minimum crystallographic free diameter of the sieving aperture equal to or greater than 4.5 Å to less than 5 Å and a maximum crystallographic free diameter to minimum crystallographic free diameter ratio of the sieving aperture from 1.1 to 1.25 (herein 10-ring pore intermediate molecular sieve).

In some embodiments, the 10-ring pore molecular sieve can have a minimum crystallographic free diameter of the of the sieving aperture equal to or greater than 5.0 Å to less than 6 Å and a maximum crystallographic free diameter to minimum crystallographic free diameter ratio of the sieving aperture of 1.0 to 1.1 (herein 10-ring pore wide molecular sieve).

In some embodiments, in the 10-ring pore molecular sieve the sieving channel is interconnected with one or more sieving and/or venting channels. In particular in some embodiments, the interconnected venting channels can be one or more 10-ring pore channels or one or more 8-ring pore channels. In some embodiments, one or more venting channels can be a 10-ring wide channel. In some embodiments, one or more venting channels can be 10-ring intermediate channel. In some embodiments, one or more venting channels can be 8-ring intermediate channel. In some embodiments, one or more venting channels can be a combination of one or more 10-ring wide channels, 10-ring intermediate channels, and 8-ring wide channels.

In preferred embodiments, the one or more sieving and/or venting channels can be interconnected to form a 2D network and/or more preferably a 3D network.

In some embodiments, the 10-ring pore molecular sieve can have a framework type selected from MEL, TUN, IMF, MFI, OBW, MFS and TER. In particular, molecular, 10-ring pore molecular sieve can be MEL or MFI.

In some embodiments, the 10-ring pore molecular sieve has a MFI framework having a sieving channel and a venting 10-ring channel. In some embodiments, the 10-ring pore molecular sieve has an OBW framework with a sieving channel and one or more venting channels that are 8-ring channels.

In some embodiments, the 10-ring pore molecular sieve has a MEL framework, having equally wide-10-ring sieving channels interconnected in all three crystallographic directions (the crystallographic free diameters are 5.3 Å×5.4 Å for all of the channels). In some embodiments, the 10-ring pore molecular sieve has a TUN framework with a wide-10-ring sieving channel (5.5 Å×5.6 Å) and a wide-10-ring venting channel (5.4 Å×5.5 Å), interconnected to create a three dimensional interconnected system. In some embodiments, the 10-ring pore molecular sieve has a IMF framework with a 5.5 Å×5.6 Å sieving channel and a number of venting channels that are all wide-10-ring channels (ranging from 5.3 Å×5.9 Å to 4.8 Å×5.4 Å) that provide a highly accessible three dimensional network. In some embodiments, the 10-ring pore molecular sieve has a MFI framework with, which has a wide-10-ring sieving channel (5.3 Å×5.6 Å) and a wide-10-ring venting channel (5.1 Å×5.5 Å), which create a three dimensional interconnected system. In some embodiments, the 10-ring pore molecular sieve has a OBW framework with a 5.0 Å×5.0 Å sieving channel that is interconnected with 8-ring venting channels (the most open of which is 3.4 Å×3.4 Å). In some embodiments, In some embodiments, the 10-ring pore molecular sieve can therefore preferably have a MEL, TUN, IMF, MFI or OBW frameworks in relation to maintaining the accessibility of the sieving channels.

In some embodiments, the 10-ring pore molecular sieve has a TER framework with a wide-10-ring sieving channel (5.0 Å×5.0 Å) and intermediate-10-ring venting channel (4.8 Å×7.0 Å). In some embodiments, the 10-ring pore molecular sieve has a MFS framework with a wide-10-ring sieving channel (5.1 Å×5.4 Å) with the ability of obstructing molecules to move out of the sieving channel being limited by the size of the opening to the 8-ring venting channel (3.3 Å×4.8 Å).

In methods herein described, the 10-ring pore molecular sieve having a T1/T2 ratio≥20:1 wherein T1 is an element independently selected from Si, and Ge, and T2 is an element independently selected from Al, B, and Ga.

In some embodiments, the 10-ring pore molecular sieve can have a T1/T2 ratio between 20:1 and 50:1, between 50:1 and 80:1 or between 80:1 and 100:1, or between 100:1 and 400:1. In some embodiments, in the 10-ring pore molecular sieve T1 can be Si. In some embodiments the 10-ring pore molecular sieve is a zeolite and T1 is Si and T2 is Al.

In methods and systems herein described, the 10-ring pore molecular sieve can further have a counterion selected from $NH_4^+$, $Na^+$, $K^+$ and $Ca^{++}$. In particular in some embodiments, the counterions can be $Na^+$ and $K^+$.

In some embodiments, the 10-ring pore molecular sieve can be ZSM-5, ZSM-11 or SUZ-4.

In some embodiments the molecular sieve can have a water content. In particular in some embodiments, the 10-ring pore molecular sieve can further have a water content up to 8% wt. In some embodiments the molecular sieve can have a water content from 0.1% to 5%. In some embodiments the molecular sieve can have a water content from 0.1% wt to 2% wt. In some embodiments the molecular sieve can have a water content from 0.1% wt to 1% wt.

In methods herein described, contacting the hydrocarbon mixture with the 10-ring pore molecular sieve herein described is performed a temperature of −20° C. to 60° C. In particular, in some embodiments, the contacting can be performed between −20° C. to 0° C. in some embodiments, the contacting can be performed between −20° C. to 25° C. In some embodiments, the contacting can be performed between 25° C. to 60° C. In some embodiments, the contacting can be performed at room temperature (between 20° C. to 25° C.).

In methods herein described, contacting the hydrocarbon mixture with the 10-ring pore molecular sieve herein described is performed for a time and under conditions to obtain a sieved hydrocarbon mixture comprising the eight-membered monocyclic unsaturated hydrocarbon component at a sieved concentration $C_s > C_i$. For example, in some embodiments, an eight-membered monocyclic unsaturated hydrocarbon at an initial concentration $C_i$=70% with methods herein described can be included in a sieved hydrocarbon mixture at a $C_s$=85.2%. In some embodiments, an eight-membered monocyclic unsaturated hydrocarbon at an initial concentration $C_i$=80% with methods herein described can be included in a sieved hydrocarbon mixture at a $C_s$=99.2%. In some embodiments, an eight-membered monocyclic unsaturated hydrocarbon at an initial concentration $C_i$=99.2% with methods herein described can be included in a sieved hydrocarbon mixture at a $C_s$=99.9%. An exemplary eight-membered monocyclic unsaturated hydrocarbon is provided by cis,cis,1,5-cyclooctadiene which can have a $C_i$ of 80% to 99.25 and can have a $C_s$ of 99.3% to 99.9%, or a $C_s$ of 99.91 to 99.99% wt.

In particular, in some embodiments, contacting the hydrocarbon mixture with the 10-ring pore molecular sieve can be performed under an inert atmosphere and in particular under nitrogen or argon. In particular, in some embodiments, contacting the hydrocarbon mixture with the 10-ring pore molecular sieve can be performed under oxygen-free conditions.

In some embodiments, methods and systems herein provided comprise reacting precursors of the eight-membered monocyclic unsaturated hydrocarbon to provide to provide the eight-membered simple-ring cyclic olefinic hydrocarbon component in the hydrocarbon mixture herein described which is a hydrocarbon mixture comprising $C_8H_{2m}$ nonlinear olefinic hydrocarbons with 4≤m≤8.

Precursors of an eight-membered monocyclic unsaturated hydrocarbons herein described comprise 1,3-butadiene, acetylene (also known as ethyne), 1,5-hexadiene, barrelene, cis,1,2-divinylcyclobutane, and 1,9-decadiene.

Reactions that can result in an eight-membered monocyclic unsaturated hydrocarbon herein described comprise nickel catalyst mediated dimerization, nickel cyanide/calcium carbide mediated tetramerization, photolysis of barrelene, catalyzed Cope rearrangement, uncatalyzed Cope rearrangement, partial hydrogenation of an eight-membered monocyclic unsaturated hydrocarbon, and ring-closing metathesis.

For example, in some embodiments, performing nickel catalyst mediated dimerization of 1,3-butadiene provides an first hydrocarbon mixture of cis,cis,1,5-cyclooctadiene, 4 vinyl-1-cyclohexene and cis-1,2-divynil-cyclo butane. Hydrogenation of the first hydrocarbon mixture results in a second mixture cis, cyclooctene ethyl-cyclohexane, cyclooctane and 1,2 diethyl cyclobutane. The first mixture or the second mixture can then be contacted with a 10-ring pore molecular sieve herein described to obtain a sieved mixture wherein either the cis,cis,1,5-cyclooctadiene (sieved first mixture) or a eight-membered monocyclic unsaturated hydrocarbon component comprising cis, cyclooctene and cyclooctane (sieved second mixture).

In embodiments herein described the methods of the disclosure, result in a hydrocarbon mixture wherein the eight-membered monocyclic unsaturated hydrocarbon is comprised at a separation concentration of at least 99.3% wt and possibly at least 99.5% wt, at least 99.7% wt, at least 99.8% wt or at least 99.9% wt. Concentration of an eight-membered monocyclic unsaturated hydrocarbon can be measured by proton NMR or gas chromatography (GC) or additional techniques identifiable by a skilled person.

In some embodiments, methods and systems herein described allow production of a hydrocarbon mixture comprising cis,cis,1,5-cyclooctadiene at least 99.3% wt and possibly at least 99.5% wt, at least 99.7% wt, at least 99.8% wt or at least 99.9% wt. In some embodiments, methods and systems herein described allow production of a hydrocarbon mixture comprising cis, cis, 1, 5-cyclooctadiene 99.9%.

In some embodiments, the sieved hydrocarbon mixture can be further reacted with other reagents to remove one or more undesired compounds from the mixture. For example, in some embodiments the sieved hydrocarbon mixture can be further contacted with a synthetic magnesium silicate (such as commercially available Magnesol®) at room temperature to selectively remove peroxides and hydroperoxides present in the sieved mixture (see Nickel et al., *Topics in Catalysis*, 2012, 55(7-10), 518-523). When exposed to air, eight-membered monocyclic unsaturated hydrocarbon react with oxygen and thus form peroxides and/or hydroperoxides at trace levels. Therefore, in some embodiments, synthetic magnesium silicates can be used in combination with a molecular sieve to further purify an eight-membered monocyclic unsaturated hydrocarbon and in particular an eight-membered monocyclic cycloolefin.

In some embodiments, the sieved hydrocarbon mixture herein described can be used in various reactions and chemical processes starting from eight-membered monocyclic unsaturated hydrocarbons, such as ring-opening metathesis polymerizations to synthesize functional polymers and complexation with transition metals (such as nickel, ruthenium, iridium) to form metathesis catalysts, hydrogenation catalysts for unsaturated compounds and polymers, carbon-carbon bond forming catalysts, and carbon-hydrogen bonding activating catalyst. In some embodiments, sieved hydrocarbon mixture can be subjected to oxidation reaction using ozone, followed by further chemical transformations to intermediates such as cycloketones, cyclic oximes, cyclic lactams, and linear functional eight-carboned compounds that can be further used to synthesize intermediates and products for agricultural, pharmaceutical, and textile industries. In particular, in some embodiments sieved eight-membered monocyclic unsaturated hydrocarbons can be used to synthesize caprolactam, which can be polymerized and form Nylon 8 polymers or be used to synthesize polyurethane polymers. For example in embodiments where the sieved hydrocarbon mixture includes eight membered monocyclic olefins, additional reactions comprise ring-opening polymerizations to synthesize functional polymers and complexation with transition metals to prepare catalysts or intermediates for such catalysts.

In particular, in exemplary embodiments, wherein the eight-membered monocyclic olefin is 1,3,5,7-Cyclooctatetraene (compound 7 or COT), the 1,3,5,7-Cyclooctatetraene can react with potassium metal to form the corresponding salt K2COT in which the COT exists as an aromatic dianion. In additional exemplary embodiments, 1,3,5,7-Cyclooctatetraene reacts with suitable transition metals to form corresponding organometallic complexes sandwich compounds such as U(COT)2 (uranocene), and Fe(COT)2.

Additional reactions that can be performed with sieved hydrocarbon mixture including eight membered monocyclic olefins, comprise ring-opening polymerizations to synthesize functional polymers and complexation with transition metals to prepare catalysts or intermediates for such catalysts.

In some embodiments, the sieved hydrocarbon mixture herein described can be used in polymerization processes. In particular in some embodiments a sieved hydrocarbon mixture and in particular a hydrocarbon mixture comprising a suitable eight-membered monocyclic unsaturated hydrocarbon at least 99.3% wt and possibly at least 99.5% wt, at least 99.7% wt, at least 99.8% wt or at least 99.9% wt can be contacted with a polymerization catalyst for a time and under condition to allow the eight-membered monocyclic unsaturated hydrocarbon to polymerize thus forming the hydrocarbon polymer.

In some embodiments, the sieved hydrocarbon mixture can be treated with a synthetic magnesium silicate to eliminate undesired interference with the catalyst by peroxides and hydroperoxides before contacting the sieved hydrocarbon mixture with the polymerization catalyst. In some of those embodiments pretreating with a synthetic magnesium silicate can results in a polymerization reaction with a lower required catalyst loading and a better conversion of the sieved hydrocarbon mixture.

In several embodiments, a hydrocarbon polymer can be provided starting from a hydrocarbon mixture of $C_8H_{2m}$ hydrocarbons with $4 \leq m \leq 8$, the hydrocarbon mixture comprising an eight-membered monocyclic unsaturated hydrocarbon at an initial concentration $C_i$ together with at least one additional nonlinear unsaturated $C_8H_{2m}$ hydrocarbons with $4 \leq m \leq 8$ compound.

In the method, the hydrocarbon mixture is contacted with a 10-ring pore molecular sieve herein described at a temperature of −20° C. to 60° C. for a time and under conditions to provide a sieved hydrocarbon mixture comprising the eight-membered monocyclic unsaturated hydrocarbon at a separation concentration Cs higher than the initial concentration $C_i$. In particular in some embodiments, the separation concentration Cs can be $C_s ? 99.3\%$ wt.

In some embodiments, the contacting of the hydrocarbon mixture with a 10-ring pore molecular sieve herein described can be performed by a selective sieving process carried out in a continuous manner. In particular in some embodiments, a stream of hydrocarbon mixture can be continuous fed into a fluidized bed packed with a 10-ring pore molecular sieve herein described or a column packed with a desired 10-ring pore molecular sieve herein described to remove the undesired components and the exit hydrocarbon mixture stream can be fed into a subsequent polymerization reactor along with streams of other components required in the polymerization reaction, such as a solvent, one or more catalysts, one or more chain-transfer agents (CTAs). In some embodiments, the exit hydrocarbon mixture stream can be also split and fed into more than one continuous polymerization reactors to perform multi-stage polymerization reactions of sieved unsaturated hydrocarbons and in particular sieved cycloolefins. The resulting sieved hydrocarbon mixture contacted with a polymerization catalyst for a time and under condition to allow the eight-membered monocyclic unsaturated hydrocarbon to polymerize thus forming the hydrocarbon polymer.

In some embodiments, the resulting sieved eight-membered monocyclic unsaturated hydrocarbon's stream is met with a stream of a polymerization catalyst solution in a solvent suitable for the polymerization reaction at the entrance of a plug-flow type reactor (or a cylindrical-shaped reactor packed with static mixers) which allows sufficient mixing of the streams and the eight-membered monocyclic unsaturated hydrocarbon to polymerize thus forming the hydrocarbon polymer. Optionally a stream of functional CTA solution can be fed into the reactor if telechelic hydrocarbon polymers are the desired products. The volume and temperature of the polymerization can be determined using the kinetics data of the polymerization reaction and the projected production rate. In the case all interfering impurities in the eight-membered monocyclic unsaturated hydrocarbon stream are completely sieved before the stream enters the polymerization reactor, a lower catalyst loading is needed and higher reaction rate can be observed, and as a result the polymerization reactor can be more compact, as will be understood by a skilled person.

In some embodiments, the polymerization reactor can provide sufficient mixing of the eight-membered unsaturated hydrocarbon stream with the catalyst solution and optionally the functional CTA solution streams, and the combined stream exiting the polymerization reactor enters collection vessels where the polymerization reaction goes to completion. In some embodiments, telechelic polymers of weight-average molecular weight≥400 kg/mol are desired products, and the corresponding polymerization is performed in a two-stage manner, which requires a two-stage reactor as the polymerization reactor.

In some embodiments, the sieved eight-membered monocyclic unsaturated hydrocarbon stream can be split and fed into both the first and the second stages at desired flow rates. The eight-membered monocyclic unsaturated hydrocarbon stream entering the first stage is met with the catalyst solution stream and the functional CTA solution stream at the entrance, and the catalyst reacts with the eight-membered monocyclic unsaturated hydrocarbon and the CTA in the first stage reactor to form a macro chain-transfer agent (MCTA) stream. The volume of the first-stage reactor is selected to provide sufficient retention time that allows <5% of the functional CTA to remain unreacted in the exit MCTA stream. The sieved eight-membered monocyclic unsaturated hydrocarbon stream entering the second-stage reactor is met with the MCTA stream, and optionally a solvent stream and catalyst solution stream at the entrance of the second-stage reactor, and the combined stream forms a chain-extension reactive mixture inside the second-stage reactor. The volume of the second-stage reactor is selected to provide complete mixing for the entering streams. The combined stream exiting the second-stage reactor is collected subsequently in vessels, where the polymerization reaction goes to completion.

In some embodiments the hydrocarbon mixture is continuously passed through a sieving unit packed with a 10-ring pore molecular sieve, and the exiting sieved mixture is fed into a fluidized bed packed with a synthetic magnesium silicate or a column packed with a synthetic magnesium silicate to selectively remove peroxides and hydroperoxides from the sieved olefin mixture stream. In some embodiments, after peroxides and hydroperoxides are removed by a synthetic magnesium silicate the sieved olefin mixture stream is fed into a desiccating unit in order to remove moisture introduced into the olefin mixture by treating the olefin mixture with a synthetic magnesium silicate that is not desiccated prior to use In some embodiments of the methods and systems herein described, use of a sieved hydrocarbon mixture comprising an eight-membered monocyclic unsaturated hydrocarbon allows performing polymerization while minimizing impurity-related interference with catalyst in the polymerization of sieved eight-membered monocyclic unsaturated hydrocarbon and leads to desired effects such as a lower required catalyst loading, better control on the monomer conversions and molecular weights of the resulting polymers, and lower production cost of polymers from sieved cycloolefins. An exemplary polymerization process starting from a hydrocarbon mixture in the sense of the present disclosure is the ring-opening metathesis polymerization of sieved cis,cis-1, 5-cyclooctadiene (COD) in the presence of a functional chain-transfer agent (CTA), as will be understood by a skilled person in the art (Example 3 and Example 6).

Methods and systems herein described allow in some embodiments performing a separation which is useful for obtaining various unsaturated eight-membered monocyclic unsaturated hydrocarbons and in particular, eight-membered monocyclic olefins with arbitrarily low concentrations of any of the hundreds of isomers of identical molar mass, but with topology that includes three to six membered rings and branched acyclic olefins. The separation can be performed under conditions that preserve the unsaturation of unsaturated hydrocarbon and in particular cycloolefins for their use as chemical intermediates or ligands. Use of molecular sieves that have low catalytic activity permits recovery of the separated olefins in a form that is free of simple ring olefins.

In some embodiment, hydrocarbon mixtures, 10-ring pore molecular sieves, precursor of eight-membered monocyclic unsaturated hydrocarbon, additional reagents to perform the reaction resulting in eight-membered monocyclic unsaturated hydrocarbon, one or more polymerization catalysts and/or synthetic magnesium silicate can be included in one or more systems to perform methods herein described. In some embodiments, the systems can be provided in the form of combination or kit of parts.

Additional materials and related methods and systems, comprising for example kit of parts or related material herein described, comprising suitable reagents, vehicles or compositions, are identifiable by a skilled person upon reading of the present disclosure.

In particular, further details concerning the hydrocarbon mixtures, catalysts and molecular sieves and generally manufacturing and packaging of the compositions and/or the kit, can be identified by the person skilled in the art upon reading of the present disclosure.

EXAMPLES

The hydrocarbon molecules, molecular sieves and related hydrocarbon mixtures, materials compositions, methods and systems herein described are further illustrated in the following examples, which are provided by way of illustration and are not intended to be limiting.

The following experimental procedures and characterization data ($^1$H and, GPC) were used for all compounds and their precursors exemplified herein.

General Information.

Chemical shifts for both $^1$H and $^{13}$C spectra are reported in per million (ppm) relative to Si(CH3)4 ($\delta$=0) and referenced internally to the proteo solvent resonance.

Materials and Methods.

All chemical reagents were obtained at 99% purity from Sigma-Aldrich, Alfa Aesar, or Mallinckrodt Chemicals. Magnesol® XL was purchased from The Dallas Group of America, Inc. $^1$H-NMR spectra were obtained using a Varian Inova 500 spectrometer (500 MHz); all spectra were recorded in CDCl$_3$. Chemical shifts were reported in parts per million (ppm) and were referenced to residual proteo-solvent resonances. Deuterated solvent used for $^1$H-NMR experiments (CDCl$_3$) was purchased from Cambridge Isotope Laboratories.

Example 1: Removal of VCH from cis,cis-1,5-cyclooctadiene Using Conventional Process In an exemplary conventional purification procedure, redistilled-grade cis,cis-1,5-cyclooctadiene (COD, 72.3 g, 0.67 mol) containing trace amount ($\leq$0.4 wt %) of 4-vinyl-1cyclohexene was syringe-transferred to a 250 ml Schlenk flask in an ice bath at 0° C. under argon atmosphere. Under argon flow, 1-Molar borane-tetrahydrofuran complex in THF (BH$_3$.THF, 108 mL, 0.11 mol) was slowly added into the flask through an additional funnel over a period of 10 minutes. The flask was taken out of the ice bath, and left to stir under argon atmosphere at room temperature for 2 hrs. Remaining COD was vacuum-distilled off the reaction mixture at 40° C. and 100 mTorr.

Figure 4:
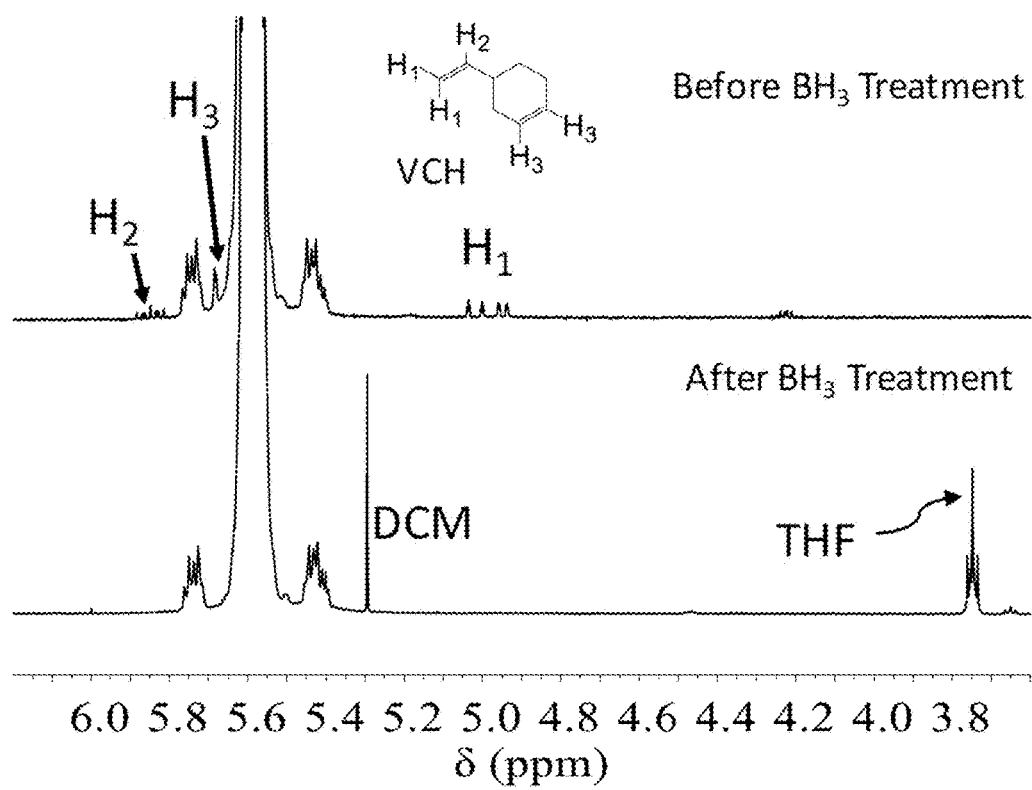
FIG. 4 shows proton NMR spectra of a mixture of COD and VCH before and after borane-tetrahydrofuran ($BH_3.THF$) treatment using conventional procedure.

Proton NMR spectrum of the resulting COD shows the concentration of VCH is below the detection limit of NMR (~50 ppm) and some residual THF as shown in FIG. 4. The amount of residual THF in COD was further reduced by subjecting the VCH-free COD to reduced pressure (100 mTorr) at room temperature for 24 hrs, and proton NMR analysis showed the concentration of THF was below 500 ppm. The yield of COD after evaporation of THF was 58%.

Figure 5:
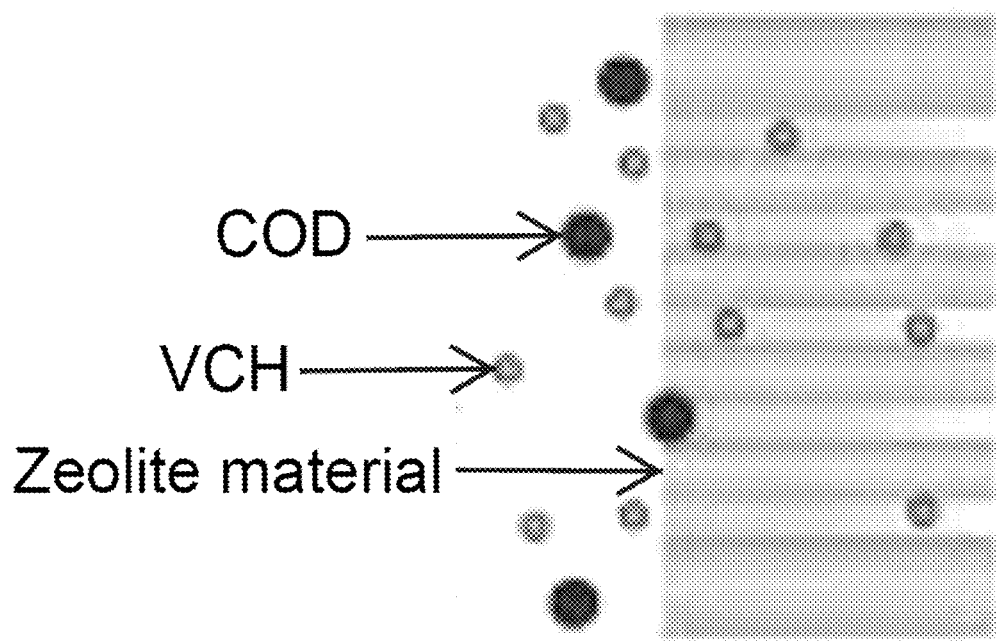
FIG. 5 shows a schematic illustration of an exemplary implementation of methods herein described wherein the schematically that VCH passes through pore opening of a zeolite and was trapped retained inside the pores, in contrast COD is not absorbed into the pores of the same zeolite, causing removal and separation of VCH from a mixture containing COD and VCH.

It was therefore concluded that the VCH passes through pore opening of a zeolite and was trapped retained inside the pores, in contrast COD is not absorbed into the pores of the same zeolite, causing removal and separation of VCH from a the initial mixture containing COD and VCH as schematically illustrated in FIG. 5. Accordingly the sieving process resulted in a sieved mixture enriched in COD as will be understood by a skilled person.

Example 3: Selective Adsorption of VCH from COD by a ZSM-5 Zeolite

Redistilled-grade cis,cis-1,5-cyclooctadiene (COD, 100 ml) containing trace amount ($\leq$0.4 wt %) of 4-vinyl-1cyclohexene (VCH) was syringe-transferred to a 250 ml Schlenk flask containing 10 grams of non-dried ZSM-5 (Si/Al=50, ammonium counterions) under argon atmosphere. The mixture was stirred under argon atmosphere at room temperature for 12 hrs.

Figure 6:
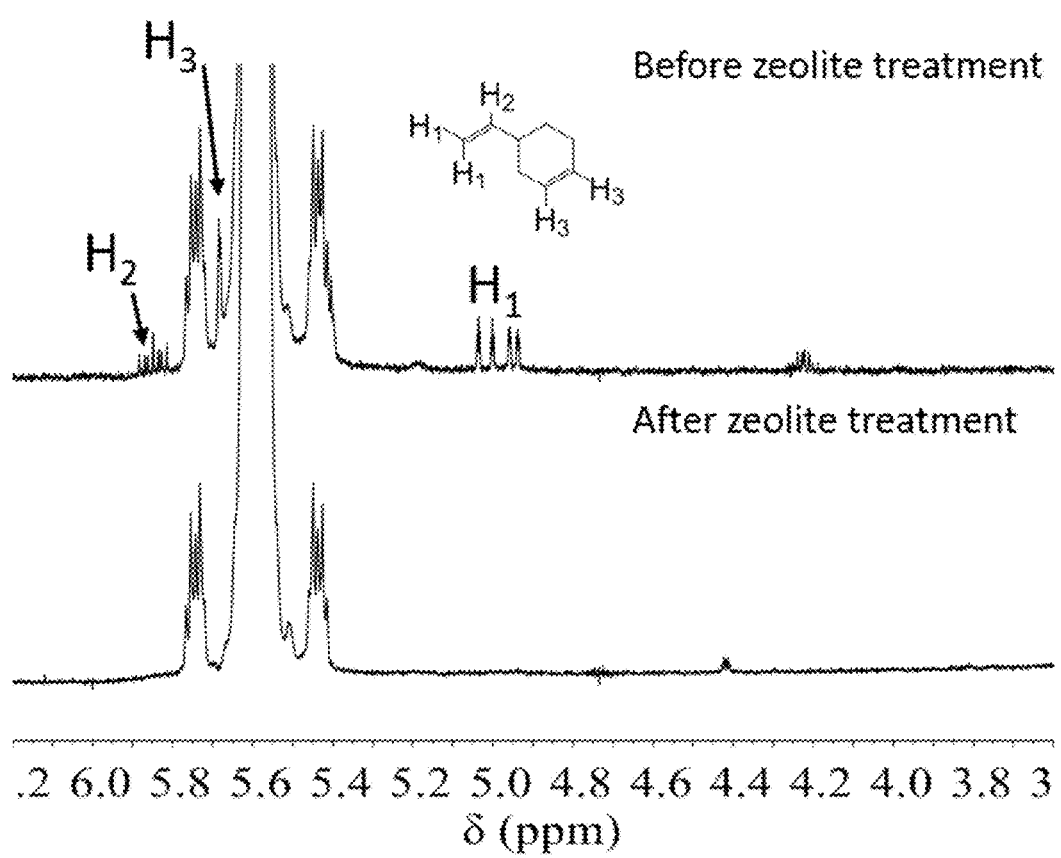
FIG. 6 shows proton NMR spectra of a mixture of COD and VCH before and after zeolite ZSM-5 treatment according to some embodiments of the present disclosure.

The liquid was vacuum-distilled off from the mixture at 35° C. and 100 mTorr, and the yield was 96%. Proton NMR analysis of the distillate showed no detectable presence of VCH in COD as illustrated in FIG. 6. The cost of treating the given amount of COD with the selected zeolite is <50% of that of the same amount of monomer.

Example 4: ROMP of COD Purified by ZSM-5 Treatment

Figure 7:
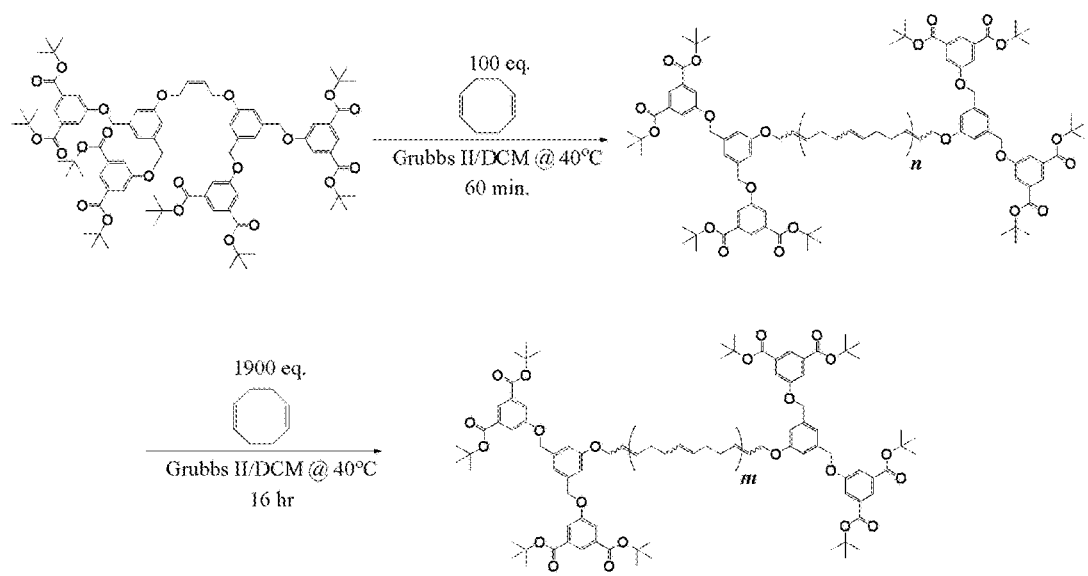
FIG. 7 shows a schematic illustration of a synthesis of di-TE PCOD via two-stage ROMP of COD as the benchmark reaction for the influence of the purity of VCH-free COD.
Figure 8:
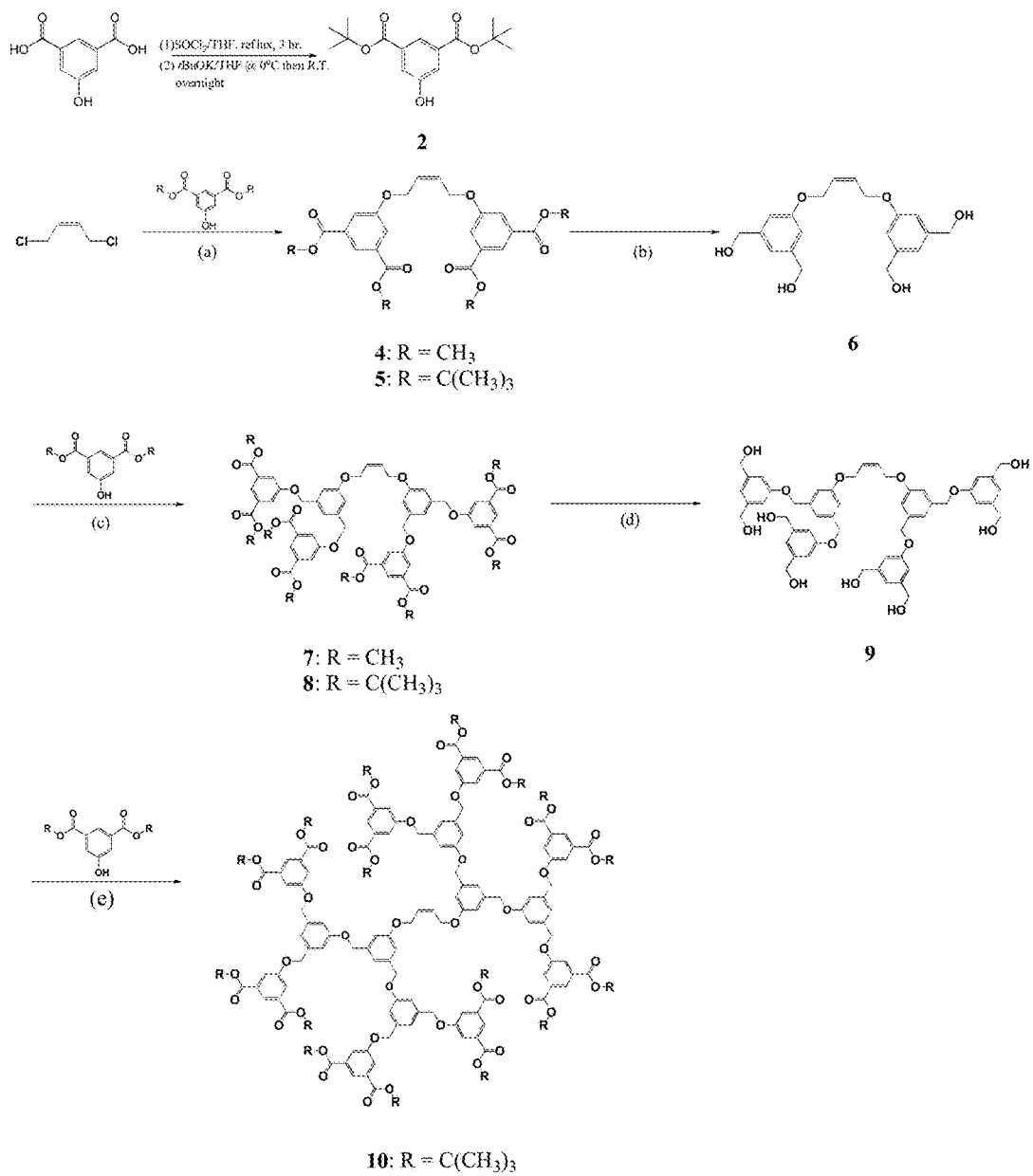
FIG. 8 shows a synthesis of a CTA with only one tert-butyl ester on each side (compound 10), with the conditions being: (a) 2.2 eq. of 2 or 2', $K_2CO_3$, N,N-dimethylformamide (DMF), 80° C., 5 h; (b) 4 eq. of $LiAlH_4$, THF, R.T., overnight; (c) 6 eq. of 2 or 2', 6 eq. of $PPh_3$, 6 eq. of DIAD, THF, 0° C. then 40° C., overnight; (d) 8 eq. of $LiAlH_4$, THF, R.T., overnight; (e) 12 eq. of 3, 12 eq. of $PPh_3$, 12 eq. of DIAD, THF, 0° C. then 40° C., overnight.

Synthesis of di-TE PCOD (FIG. 7) was selected to test the performance of ZSM-5 treated COD in two-stage ROMP in the presence of a di-TE CTA (compound 8 in FIG. 8). VCH-free COD was prepared according to the purification procedure described above in Example 3. A total COD-to-CTA ratio of 10,000:1 was used, and 100 equivalents of COD was used in the first-stage reaction, macro-CTA synthesis, where a 30:1 CTA-to-Grubbs II ratio was used. Specifically, 5.4 mg of the di-TE CTA (3.7 µmol) was dissolved in 1 mL of degassed dichloromethane (DCM) in a 100-mL Schlenk flask under argon atmosphere, followed by the addition of 0.04 g of ZSM-5 treated COD (366 µmol) and 0.1 mL of 1 mg/mL Grubbs II solution in DCM. The mixture was stirred at 40° C. for 1 hr. 3.96 g of ZSM-5 treated COD (36.2 mmol) along with 8 mL of degassed DCM were added to the Schlenk flask to start the chain extension reaction. 5 minutes later, an aliquot was taken for NMR analysis, and 50 mL of oxygenated DCM was added into the flask to terminate the reaction. Proton NMR analysis showed the conversion of COD was 50%, and gel-permeation chromatography analysis in conjunction with multi-angel laser light scattering (GPC-MALLS) showed the weight-average molecular weight ($M_w$) of the resulting di-TE PCOD was 1,050 kg/mol (PDI=1.5). Under same conditions and conversion of COD, $BH_3$.THF treated COD could only afford an $M_w \leq 500$ kg/mol. A skilled person will understand that purifying COD with ZSM-5 improves control of molecular weight in the ROMP procedure, which cannot be achieved in ROMP of COD treated with BH3 THF.

Example 5: Removal of Peroxides and Hydroperoxides from ZSM-5 Treated COD 100 mL of ZSM-5 treated COD from Example 3 was stirred with 10 grams of oven-dried synthetic magnesium silicate, Magnesol®-XL, under argon atmosphere at room temperature for 12 hours to remove peroxides and hydroperoxides from the olefin. The liquid was separated from the adsorbent via vacuum distillation at 35° C. with a yield≥95%. The cost is <1% the cost for the same amount of monomer. Magnesol®-XL treatment improves activity of catalyst and thus conversion of COD in ring-opening metathesis process.

Example 6: Comparative Study of ROMP of COD Treated with BH3.THF/5/Magnesol®-XL and ZSM-5/Magnesol®-XL Procedures To demonstrate the advantage of the invented method of selective adsorption of undesired unsaturated hydrocarbons from a desired eight-membered monocyclic unsaturated hydrocarbon, VCH-free COD was prepared according to the purification procedure described above in Examples 3 and 5, and the method of selective chemical consumption of VCH by $BH_3$.THF described in Example 2 was used to prepare VCH-free COD as the control. The synthesis of di-DE PCOD via the two-stage ROMP of COD in the presence of a di-DE CTA, as shown below, was selected to further benchmark the performance of two different purification methods for COD:

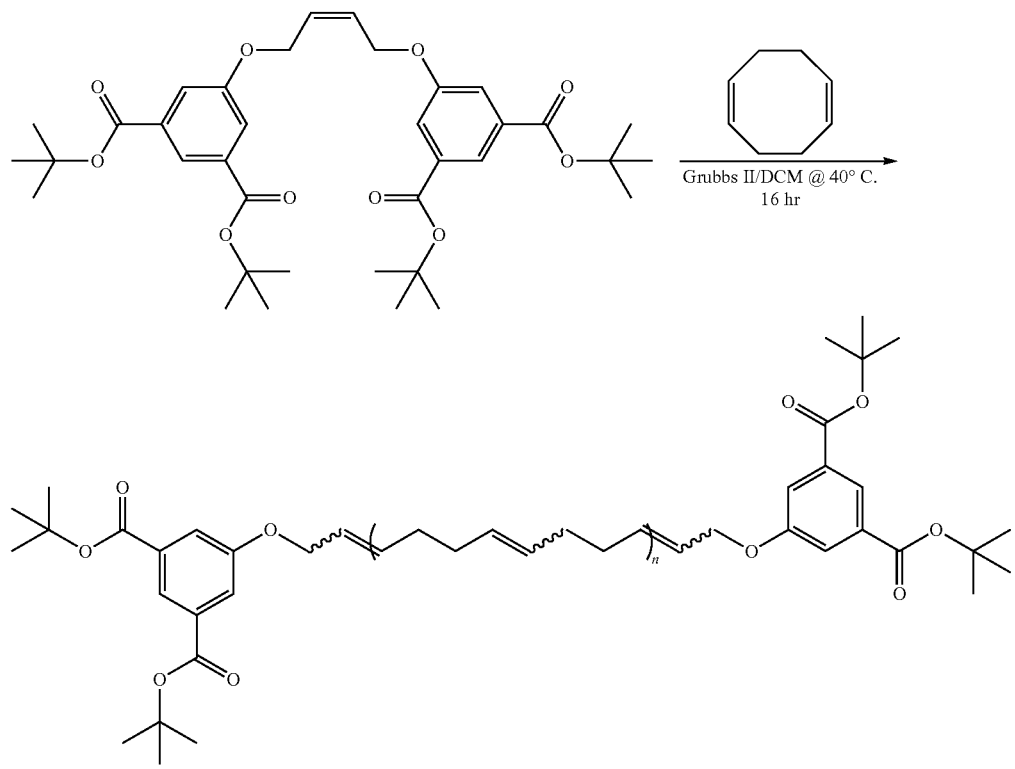

In the ROMP procedure, a total COD-to-CTA ratio of 2000:1, a total CTA-to-catalyst (here $2^{nd}$ generation Grubbs catalyst) of 30:1, and a total concentration of COD in DCM of 2.52 M were used. 50 equivalents of COD (treated with ZSM-5 and Magnesol®-xl) were used in the first stage of ROMP to react with the CTA, and the remaining 1950 equivalents of COD (treated with ZSM-5 and Magnesol®-xl) were used in the second stage reaction. Specifically, 11.7 mg of di-DE CTA was dissolved in 2 mL of degassed DCM in a 100 mL Schlenk flask, followed by the addition of 0.1 g of VCH-free COD and 0.52 mL of 1 mg/mL Grubbs II solution in degassed DCM. The mixture was stirred under argon atmosphere at 40° C. for 1 hr. 3.9 g of VCH-free COD and 6 mL of degassed DCM were subsequently added into the Schlenk flask to start the second stage chain extension reaction. The reaction mixture was left to stir at 40° C. for 15 hrs, and aliquots were taken for proton NMR and GPC-MALLS analysis. The same procedure was repeated using COD treated with $BH_3$.THF and Magnesol®-xl.

Results of the comparative study are shown in Table 1 below:

TABLE 1

| Monomer Treatment | Conv. Of COD (%) | $M_w$ (kg/mol) | PDI |
|---|---|---|---|
| $BH_3$-THF | 95 | 176 | 1.47 |
| ZSM-5 + Magnesol | 100 | 318 | 1.49 |

The ROMP procedure using COD treated with ZSM-5 and Magnesol®-xl gave 100% conversion of COD, and the $M_n$ (=$M_w$/PDI) of the resulting polymer, 213 kg/mol, agreed very well with the predicted value (i.e., molecular weight of COD×2000). On the other hand, the reaction using COD treated with BH$_3$.THF could achieve only 95% conversion of COD, and the $M_w$ of the resulting polymer was 176 kg/mol, 55% of that from the zeolite-purified COD. Besides, the $M_n$ of the resulting polymer, 120 kg/mol, did not agree with the initial COD/CTA ratio, indicating that undesired secondary metathesis reactions took place along with the primary polymerization reaction. A skilled person can understand that purifying COD with ZSM-5 and Magnesol® enables control of molecular weight in the ROMP procedure by adjusting the ratio of COD to CTA, which cannot be seen in ROMP of COD treated with BH$_3$.THF and Magnesol®-xl.

Example 7: Comparative Study of ROMP of COD Purified by ZSM-5 Alone and COD by ZSM-5/Magnesol®-xl COD was purified according to the purification procedure described above in Example 3. A portion of the zeolite-treated COD was further purified using the procedure described in Example 5. Synthesis of di-TE PCOD (FIG. 7) via two-stage ROMP in the presence of a di-TE CTA (compound 8 in FIG. 8) was selected to benchmark the performance of COD purified with ZSM-5 only and COD purified with ZSM-5 and Magnesol®-xl. A total COD-to-CTA ratio of 4,000:1 was used, and 50 equivalents of COD were used in the first-stage reaction, macro-CTA synthesis, where a 30:1 CTA-to-Grubbs II ratio was used. Specifically, 33.5 mg of the di-TE CTA (22.9 μmol) was dissolved in 3 mL of degassed dichloromethane (DCM) in a 250-mL Schlenk flask under argon atmosphere, followed by the addition of 0.125 g of COD treated with ZSM-5 only (1.14 mmol) and 0.65 mL of 1 mg/mL Grubbs II solution in DCM. The mixture was stirred at 40° C. for 30 min. 9.875 g of COD treated with ZSM-5 only (36.2 mmol) along with 22 mL of degassed DCM were added to the Schlenk flask to start the chain extension reaction. 16 hrs later, aliquots were taken for proton NMR and GPC-MALLSs analysis, and 200 mL of oxygenated DCM was added into the flask to terminate the reaction. The same polymerization procedure described here was applied to the COD purified with ZSM-5 and Magnesol®-xl. Results of the comparative study are shown in Table 2 below:

TABLE 2

| Monomer Treatment | Conv. Of COD (%) | $M_w$ (kg/mol) | PDI |
| --- | --- | --- | --- |
| ZSM-5 + Magnesol-XL | 98 | 666 | 1.50 |
| ZSM-5 Only | 90 | 650 | 1.53 |

The results in Table 2 indicate that removal of peroxides and hydroperoxides from COD using Magnesol®-xl can mitigate catalyst interference and thus improve the conversion of COD in the two-stage procedure. The benefit of and Magnesol®-xl for COD purified using ZSM-5 is much greater than the benefit of and Magnesol®-xl for COD purified using BH$_3$.THF.

Example 8: Regeneration ZSM-5

Zeolite adsorbent, ZSM-5, of example 3 is re-generated by desorption of VCH using steam treatment. The ZSM-5 of example 2 was steamed at 700° C. to 1450° F. (700° C.) for 5-15 hours in 10-45% steam/90-55% air, at atmospheric pressure to be regenerated for repeated use.

Example 9: GPC-MALLS for Characterization of Polymers

MALLS, i.e. Multi-angle Laser Light Scattering, was used in conjunction with GPC to determine the molecular weights and polydispersity of the polymers. The system used a Wyatt DAWN EOS multi-angle laser light scattering detector (k=690 nm) with a Waters 410 differential refractometer (RI) (k=930 nm) connected in series. Chromatographic separation by the size exclusion principle (largest comes out first) was achieved by using four Agilent PLgel columns (pore sizes $10^3$, $10^4$, $10^5$, and $10^6$ Å) connected in series. Degassed THF was used as the mobile phase with a temperature of 35° C. and a flow rate of 0.9 ml/min. The time for complete elution through the system was 50 min, and MALLS and RI data were recorded at 5 Hz.

Samples were prepared by dissolving 5 mg of polymer in 1 ml of THF and filtering the solution through 0.45 μm PTFE membrane syringe filters immediately before injection. An injection volume of 20 μl was used. The data were analyzed by Wyatt Astra Software (version 5.3.4) using the Zimm fitting formula with dn/dc=0.125 for PCOD in THF to obtain weight-average molecular weight ($M_w$) for each polymer reported.

Example 10: Guidance on Molecular Sieve Selection

Given the following information on silicate and aluminosilicate zeolites that possess at least one 10-ring channel given in the 6th Edition of the *Atlas of Zeolite Framework Types* the candidates for use in the present invention were identified and are listed in FIG. 9.

Wenkite is eliminated because one of the crystallographic diameters of its 10-ring channel that is less than 3 Å. Heulandite is eliminated because the ratio of its larger crystallographic diameter to its smaller crystallographic diameter is greater than 2. The following approach was then followed to select suitable molecular sieves.

A first step, Step 1) was that of identifying 10-ring, wide-pore molecular sieve frameworks. The most promising candidates were identified by selecting those that both have a minimum crystallographic free diameter that is greater than 5 Å and have pore aspect ratio less than 1.1. Ten zeolite frameworks satisfy both of these criteria: IMF, MEL, MFI, MFS, OBW, PON, SFF, STF, TER and TUN.

A second step, Step 2) was that of identifying 10-ring, wide-pore frameworks that permit diffusion in three dimensions. Among this group of ten 10-ring, wide-pore molecular sieve frameworks, four have channels that are connected in three dimensions, two have channels that are connected in two dimensions, and four only permit diffusion in one dimension. Therefore, the four most promising candidates are identified (10-ring, wide-pore molecular sieve frameworks that permit diffusion in three dimensions): MEL, MFI, OBW and TUN.

An additional optional steps (since four strong candidates have already been identified, further steps are optional) were that of: identifying 10-ring, medium-pore molecular sieve frameworks from the remaining zeolite frameworks by selecting those that both have a minimum crystallographic free diameter that is greater than 4.5 Å and have pore aspect ratio less than 1.25. Five of the remaining zeolite frameworks satisfy both of these criteria: MTT, NES, SFG, STI and TON. Among this group of five zeolite frameworks, two have channels that are connected in two dimensions, none are connected in three dimensions, and the majority only permit diffusion in one dimension. Therefore, the most promising candidates in this secondary group are NES and SFG.

A further additional optional step was that of identifying 10-ring, narrow-pore molecular sieve frameworks from the remaining zeolite frameworks by selecting those that both have a minimum crystallographic free diameter that is greater than 4 Å and have pore aspect ratio less than 1.5. Five of the remaining zeolite frameworks satisfy both of these criteria: EUO, FER, LAU, MWW and SZR.

Among this group of five zeolites, one has channels that are connected in three dimensions and one is connected in two dimensions (the majority only permit diffusion in one dimension). Therefore, the most promising candidate in the third group is SZR.

A survey of commercially available 10-ring zeolites identified suppliers for five framework structures: MEL, MFI, MTT, TON, FER and MWW. Two of these belong to the group of wide-10-ring molecular sieves that are connected in three dimensions: MEL and MFI.

The *Atlas of Zeolite Framework Types* indicates that zeolites with MEL framework have the common name ZSM-11. Vendors offer ZSM-11 with Si:Al ratios of 25, 30, 50, 80 and 280. Based on other examples in this patent, the team chose to test ZSM-11 compositions with the three highest Si:Al ratios (50, 80 and 280).

Similarly, MFI zeolites (common name ZSM-5) are available commercially with a variety of Si:Al ratios, include 50, 80 and >200. Therefore, the team ordered samples of ZSM-5 to include in a trial study to identify the best zeolite for the desired separation.

known as 5 Å, had Si:Al ratio 2:1. The Beta zeolite (BEA) with Si:Al 25:1 neutralized with ammonium. Two MOR zeolites were studied: a sodium mordenite with Si:Al of 13:1 and an ammonium mordenite with Si:Al of 20:1. The Y zeolite (FAU) had Si:Al 5.2:1.

Trial samples consisting of 1 part vinylcylohexane to 99 parts cyclooctadiene were prepared to represent the mixtures that require separation. In addition, samples with 1 part cyclooctadiene to 99 parts of cyclododecatriene (CDDT) were used for reference.

Vials were prepared with 0.5 g of zeolite and capped loosely so that gas could escape. Then the vials and zeolites were dried in a vacuum oven at 110° C. at a reduced pressure (100 mtorr) for 18 hours prior to use. Once cooled down to room temperature, the oven was filled with argon, and the vials were immediately capped tightly and taken out from the oven.

2.5 g of the test sample, either 1% VCH in COD or 1% COD in CDDT, was added to the vial. The content was magnetically stirred for 2 hours at room temperature and ambient temperature.

After two hours, approximately 0.1 ml of each sample was filtered to separate the sieved mixture from the zeolites using a 0.45 μm syringe filter. Then 5 mg of filtrate was diluted in 0.9 ml of deuterated chloroform and $^1$H NMR spectra were acquired at 500 MHz.

The signal-to-noise ratio of the $^1$H NMR spectra permitted detection of as little at 50 ppm of either VCH in COD or COD in CDDT. The outcomes of each experiment either showed essentially no reduction of the minor component or reduction below the detection limit. The $^1$H NMR spectra of the constituents that remained in the sieved mixture were unchanged relative to that constituent in the trial sample. Therefore, the results are listed in Table 3 below as "yes" the minor component was reduced below the detection limit or "no" the minor component was not removed.

TABLE 3

| Classification | Framework | Zeolite name | Si:Al | Counterion | removal of VCH from COD? | COD enters pores? |
|---|---|---|---|---|---|---|
| 8-ring | LTA | Linde A | 2 | Ca++ | No | No |
| wide-10-ring | MFI | ZSM-5 | 50 | NH4+ | Yes | No |
| | | | 80 | NH4+ | Yes | No |
| 12-ring | BEA | Beta | 25 | NH4+ | No | Yes |
| | MOR | mordenite | 13 | Na+ | No | Yes |
| | | | 20 | NH4+ | No | Yes |
| | FAU | Y | 5.2 | NH4+ | No | Yes |

Example 11: Evaluation of Zeolite Efficacy in Selective Removal of VCH from COD

A chemical process using cyclooctadiene (COD) was adversely affected by the presence of vinylcyclohexene (VCH). Commercially available redistilled-grade cyclooctadiene was found to contain more than 1000 parts per million (ppm) VCH; the process required that VCH content be less than 100 ppm.

A screening study was performed to evaluate the possibility of using the separation method of the present invention. Molecular sieves with framework MFI (ZSM-5) were chosen for testing and were purchased with two different Si:Al ratios, 50 and 80, with ammonium counterions.

For comparison, a small pore framework (LTA) and three large pore frameworks (BEA, MOR and FAU) were included in the study. The calcium Linde A zeolite (LTA), The results summarized in Table 3 confirmed that: a) a wide-10-ring zeolite with venting channels (MFI) can provide a purity of better than 99.99% COD; b) a 0.5 g amount of zeolite is sufficient to remove at least 0.025 g of VCH; c) separation can be performed at ambient temperature; and d) separation is complete within a time that is short compared to the rate of deleterious reactions at the temperature used to perform the separation.

Example 12: Effect of Water Content on Separation Effectiveness

Two ZSM-5 zeolites with Si/Al of 28:1 and 80:1 respectively were selected to demonstrate the importance of properly drying molecular sieves before contacting a hydrocarbon mixture for selective removal of undesired components. 0.5 g of each zeolite was used as received and loaded into a 20 mL vial charged with a stir bar, and 0.5 g of each zeolite was loaded in a 20 mL vial charged with a stir bar, dried at 310° C. and 100 mTorr for 20 min, cooled down to room temperature, and covered with argon atmosphere prior to use. 2.5 g of 1 wt % VCH in COD described in Example 11 was added to each of the four vials. The four mixtures were stirred at room temperature and ambient pressure for 2 hrs.

After 2 hrs, approximately 0.1 ml of each sample was filtered to separate the sieved mixture from the zeolites using a 0.45 μm syringe filter. Then 5 mg of filtrate was diluted in 0.9 ml of deuterated chloroform and $^1$H NMR spectra were acquired at 500 MHz. The signal-to-noise ratio of the $^1$H NMR spectra permitted detection of as little at 50 ppm of either VCH in COD or COD in CDDT. The results of the two zeolites dried at 310° C. and 100 mTorr prior to use show reduction of VCH concentration below the detection limit, while the results of those used as received show that the VCH concentration in the samples was reduced to ca. 0.02 wt %. The comparisons exemplified here suggest a skilled person should properly dry the molecular sieves to minimize the amount of residual water in sieving channels before contacting them with a hydrocarbon mixture, so that better separation effectiveness can be achieved without increasing molecular sieve loading.

Example 13: Determination of Water Content in a Zeolite Sample Using Thermogravimetric Analysis (TGA)

Figure 10:
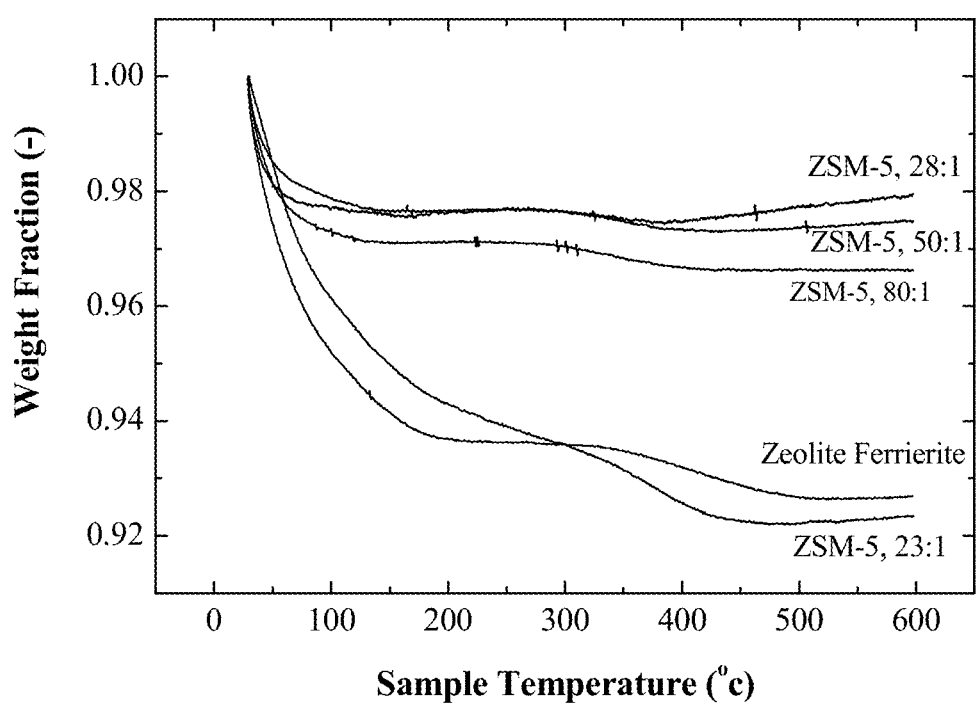
FIG. 10 shows TGA results of ZSM-5 23:1, ZSM-5 28:1, ZSM-5 50:1, ZSM-5 80:1, and zeolite ferrierite.

Thermogravimetry, as will be understood by a skilled person, is one of the effective ways to understand the water content in a zeolite sample. The following five as-received zeolite samples were analyzed on a PerkinElmer Simultaneous Thermal Analyzer (STA 6000) equipped with an autosampler: ZSM-5 with Si/Al of 23:1 (ammonium counterions), ZSM-5 with Si/Al of 28:1 (ammonium counterions), ZSM-5 with Si/Al of 50:1 (ammonium counterions), ZSM-5 with Si/Al of 80:1 (ammonium counterions), and zeolite ferrierite with Si/Al of 20:1 (ammonium counterions). Approximately 6 mg of each sample was analyzed under nitrogen flow at 20 mL/min, a heating rate of 5° C./min, and a temperature range from 30 to 600° C. The results shown in FIG. 10 indicate that there is at least a water content of 2 wt % in each zeolite sample, and that those with a Si/Al ratio below 25:1 (i.e., ZSM-5 23:1 and zeolite ferrierite) are more hydrophilic due to their relative high contents of trivalent aluminum atoms and can contain up to 8 wt % water. The comparisons demonstrated in this example provide a skilled person guidance on how to select a molecular sieve according to its Si/Al ratio, and that heating a molecular sieve at ambient pressure over 400° C. can remove water molecules from the sieving channels.

Example 14: Molecular Sieves Framework Categorization

Using data for all of the 10-ring molecular sieves documented in the 6$^{th}$ edition of the *Atlas of Zeolite Frameworks*, the 10-ring frameworks are categorized using the criteria for: 1) dimensions of the minimum aperture of the sieving channel (defined as the only 10-ring channel or the 10-ring channel that has the largest minimum crystallographic free diameter among the 10-ring channels in the framework); and B) connectivity of the one or more sieving channels together with other channels.

The framework crystallographic free diameters of the sieving pore can be accordingly categorized as:

"wide" (minimum crystallographic free diameter that is 5.0 Å or greater and less than 6 Å and ratio of maximum/minimum crystallographic free diameter is between 1.1 and 1.0), "intermediate" (zeolites that only satisfy one of the two criteria for "wide" and all zeolites that have a minimum crystallographic free diameter that is 4.5 Å or greater and less than 5.0 Å and has a ratio of maximum/minimum crystallographic free diameter between 1.1 and 1.25)

"narrow" (zeolites that only satisfy one of the two criteria for "intermediate" and all zeolites that have a minimum crystallographic free diameter that is 4.0 Å or greater and less than 4.5 Å and has a ratio of maximum/minimum crystallographic free diameter between 1.25 and 1.5).

The framework crystallographic free diameters of the sieving pore can also be categorized in view of the framework connectivity as:

"3D Sieving channel network" which indicates that the framework offers a three-dimensional network in which all channels are sieving channels.

"3D Sieving channel+Venting channels network" which indicates that the framework offers venting channels that taken together with one or more sieving channels affords a three dimensional network "2D Sieving channel+Venting channel network" which indicates that the framework offers either two sieving channels or a sieving channel with one venting channel that together provide a two dimensional network; and "1D Sieving channel" which indicates a framework in which the sieving channels do not connect with an additional dimension.

The resulting assignments are given in Table 4 below.

TABLE 4

Classification subgroups of 10-ring Frameworks

| sieving channel aperture | 3D Sieving channel network | Sieving channel + Venting channels provide a 3D network | Sieving channel + Venting channel provide a 2D network | 1D Sieving channel |
|---|---|---|---|---|
| Wide-10-ring | MEL | TUN, IMF, MFI, OBW | MFS, TER | TON, SFF, STF |
| Intermediate-10-ring | none | none | STI, SFG, NES | MTT, TON |
| Narrow-10-ring | none | SZR | FER, MWW | EUO, LAU |

This example shows how to organize a large list of possible zeolites to plan an efficient set of experiments to evaluate them for a separation of interest.

For example, the skilled person may choose to perform an initial experiment with a zeolite having at least one intermediate-width 10-ring sieving channel, the table above would guide them to choose STI, SFG or NES first. The skilled person chooses a zeolite having the NES framework in a form that has Si:Al greater than or equal to 50 and neutralized with Ca$^{++}$ (that is, an example of the NES framework with pores that are kept open by using Ca$^{++}$ rather than Na$^+$ or NH$_4$$^+$). If they observe that the molecules to be retained in the sieve do not enter this NES zeolite, they can rule out five frameworks: NES, STI and SFG because they will behave similarly to one another, and MTT and TON which will be inferior to NES, STI an SFG. If the molecules to be retained in the sieve conform to one of the Markush groups in the present invention, they will enter the pores of one of the Wide-10-ring zeolites. Therefore, discouraging results on an Ca-NES zeolite with high Si:Al indicates that the next tests should be performed on one or more zeolites that have a framework selected from of the Wide-10-ring category, preferably frameworks with venting channels. For efficiency, the skilled person might choose one zeolite of framework MEL and one from the group of TUN, IMF, MFI and OBW, initially choosing specific compositions that have Si:Al greater than or equal to 50 and neutralized with $Ca^{++}$. In this way, a very small number of experiments can be used to identify molecular sieves that perform the desired separation.

Example 15: Process to Produce Cyclooctadiene from Butadiene

In this example, 1,3-butadiene is fed to a dimerization reactor that produces two products in the proportion 67.1% wt cyclooctadiene (COD) and 23.6% wt cyclododecatriene (CDDT) per mass of butadiene consumed. In addition, it produces 1.7% wt 4-vinyl-1-cyclohexene (VCH) per mass of butadiene consumed. The VCH is difficult to separate from COD. Twice distilled COD continues to have 0.2% wt to 0.5% wt VCH and approximately half of the COD is lost to the stream that has the higher concentration of VCH. Borane treated COD can reduce the VCH to less than 0.1%; however, approximately half of the COD is lost and diverse impurities are created that poisons the catalysts in important processes for which COD is sold.

Therefore, separation using the present invention is integrated into the process of converting butadiene to products.

Figure 11:
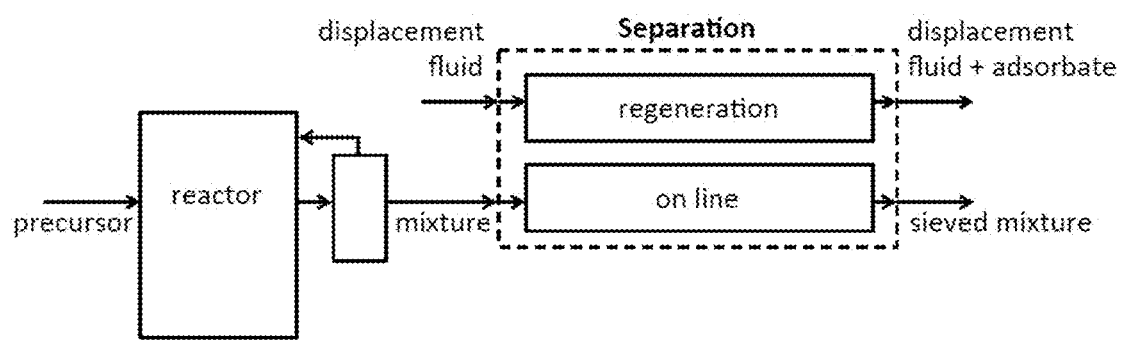
FIG. 11 shows a schematic diagram of an exemplary process to convert a precursor to a desired sieved hydrocarbon mixture.

Reference is made in this connection to the schematics of FIG. 11 showing an exemplary process that converts a "precursor" to a desired "sieved mixture" and a stream of "displacement fluid" and "adsorbate"; the precursor is introduced to a "reactor" in which desired product molecules are formed (the stream from the reactor may optionally be passed through a device that separates precursor and recycles it to the reactor); the mixture from the reactor flows into the "separation" in which at least one device with molecular sieve is "on line" and at least one device with molecular sieve is undergoing "regeneration"; the mixture that passes through the device produces a "sieved mixture" that is on line is enriched in one or more desired components and leaves adsorbate on the molecular sieves; the device that is undergoing regeneration may optionally be treated with a "displacement fluid" to recover the adsorbate in a stream of "displacement fluid+adsorbate".

As applied to this example, the precursor of the schematics of FIG. 11 is 1,3-butadiene. The 1,3-butadiene is easily recycled because it has much higher vapor pressure than VCH, COD or CDDT. The mixture is a liquid composed of VCH, COD and CDDT. When the mixture passes through the inventive molecular sieve system that can be dual bed (in which the two devices alternate between being on line and being in regeneration), or multiple bed (in which the scheduling can be designed using relationships that are known to the skilled person) or fluidized bed (in which the zeolite moves from the online device to the regeneration device). The mixture flows through a device in which the molecular sieve adsorbs the VCH at a flow rate that allows 99% of the VCH to adsorb to the molecular sieve. The composition of the sieved mixture is 73.9% COD and 26.0% CDDT and more than 99% of the COD that was present in the mixture is still present in the sieved mixture. The stream of COD and CDDT is fed to a vacuum distillation column that easily separates the two in high yield by virtue of the large difference in the boiling points of the two species (at ambient pressure, bp 151° C. for COD and bp 231° C. for CDDT). The regeneration of the molecular sieve can be performed in two ways. Regeneration without recovery of the adsorbate can be achieved simply heating the molecular sieve to vaporize the VCH and then burning off the organic vapor. Regeneration with recovery of the adsorbate can be achieved by using benzene as the displacement fluid and then using vacuum distillation to drive off benzene (at ambient pressure, boiling point (i.e. bp) 80° C. for benzene and bp 129° C. for VCH).

This example shows that the materials, methods and systems of the present invention can be used in an integral manner with a reactor the produces products that present separation challenges downstream.

The example shows that products that are destroyed or lost in prior art purifications such as sequential distillation or reactive removal of contaminant can be obtained in high yield by using the materials, methods and systems of the present invention.

Example 16: Exemplary Desorption Systems for the Molecular Sieves

Exemplary of adsorption systems for the molecular sieves of the present invention include:
Multiple-bed adsorption
Single-bed adsorption
Static adsorption
Fluidized bed adsorption
Multiple-Bed Adsorption:
Multiple bed adsorption is ideal for most commercial, large-scale fluid purification operations. Conventional fixed-bed adsorption equipment is used. For example, a dual-bed installation places one bed on-stream to purify the fluid while the other bed is being purged, either to discard or collect the adsorbate. When the process design requires a shorter adsorption time than the purge time, additional beds can be added to permit continuous processing of the feed.

Single-Bed Adsorption:
Single-bed adsorption can be used when interrupted product flow is acceptable. When the adsorption capacity of the bed is reached, it can be regenerated. The regenerated bed can be used for another batch in the same process or used for a batch of a different material or even moved to another location where it is needed.

Static Adsorption:
When manufactured into various physical forms, molecular sieves can be used as static adsorbents in closed liquid systems.

Fluidized-Bed Adsorption:
Fluidized bed-adsorption can be used to provide continuous regeneration of zeolite that is saturated with adsorbate by directing a stream of suspended zeolite particles at the bottom of a fluidized adsorption column to the top of a regeneration column and replenishing the zeolites in the fluidized bed using a stream of zeolite suspension that has been completely regenerated directed from the bottom of the regeneration column to the top of the fluidized adsorption bed.

The examples set forth above are provided to give those of ordinary skill in the art a complete disclosure and description of how to make and use the embodiments of the hydrocarbon mixtures, eight membered unsaturated hydrocarbons, nonlinear unsaturated $C_8H_{2m}$ hydrocarbons with $4 \leq m \leq 8$, polymers, compositions, systems and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually.

It is to be understood that the disclosures are not limited to particular compositions materials, or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

Unless otherwise indicated, the disclosure is not limited to specific reactants, substituents, catalysts, reaction conditions, or the like, as such may vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "a polymer" includes a single polymer as well as a combination or mixture of two or more polymers, reference to "a substituent" encompasses a single substituent as well as two or more substituents, and the like.

As used in the specification and the appended claims, the terms "for example," "for instance," "such as," or "including" are meant to introduce examples that further clarify more general subject matter. Unless otherwise specified, these examples are provided only as an aid for understanding the applications illustrated in the present disclosure, and are not meant to be limiting in any fashion.

In this disclosure and in the claims that follow, reference will be made to a number of terms, which shall be defined to have the following meanings:

The term "alkyl" as used herein refers to a linear, branched, or cyclic saturated hydrocarbon group typically although not necessarily containing 1 to about 10 carbon atoms, preferably 1 to about 6 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 6 carbon atoms. The term "cycloalkyl" intends a cyclic alkyl group, typically having 4 to 12, preferably 5 to 8, carbon atoms. The term "substituted alkyl" refers to alkyl substituted with one or more substituent groups of hydrocarbons, If not otherwise indicated, the terms "alkyl" and "lower alkyl" include linear, branched, cyclic, unsubstituted, substituted, alkyl and lower alkyl, respectively.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Exemplary aryl groups contain one aromatic ring e.g., phenyl.

The terms "cyclic" and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic.

The term "olefins" as used herein indicates two carbons covalently bound to one another that contain a double bond ($sp^2$-hybridized bond) between them.

By "substituted" as in "substituted alkyl," "substituted aryl," and the like, as alluded to in some of the aforementioned definitions, is meant that in the, alkyl, aryl, or other moiety, at least one hydrogen atom bound to a carbon atom is replaced with one or more hydrocarbon groups.

Examples of such substituents include, without limitation: functional groups such as and the hydrocarbyl moieties $C_1$-$C_6$ alkyl (preferably $C_1$-$C_4$ alkyl), $C_2$-$C_6$ alkenyl (preferably $C_2$-$C_4$ alkenyl), $C_2$-$C_6$ alkynyl (preferably $C_2$-$C_4$ alkynyl), $C_6$ aryl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

In the molecular structures herein, the use of bold and dashed lines to denote particular conformation of groups follows the IUPAC convention. A bond indicated by a broken line indicates that the group in question is below the general plane of the molecule as drawn, and a bond indicated by a bold line indicates that the group at the position in question is above the general plane of the molecule as drawn.

The term "carbon chain" as used herein indicates a linear or branched line of connected carbon atoms.

Although any methods and materials similar or equivalent to those described herein can be used in the practice for testing of the specific examples, additional appropriate materials and methods are described herein.

A number of embodiments of the disclosure have been described. Nevertheless, it will be understood that various modifications may be made without departing from the spirit and scope of the present disclosure. Accordingly, other embodiments are within the scope of the following claims.

What is claimed is:

1. A sieved hydrocarbon mixture obtained by separating an eight-membered monocyclic unsaturated hydrocarbon from a hydrocarbon mixture further comprising additional nonlinear unsaturated $C_8H_{2m}$ hydrocarbons with $4 \leq m \leq 8$, wherein separating the eight-membered monocyclic unsaturated hydrocarbon comprises providing a 10-ring pore molecular sieve having a sieving channel with a 10-ring sieving aperture with a minimum crystallographic free diameter greater than 3 Å and a ratio of the maximum crystallographic free diameter to the minimum crystallographic free diameter between 1 and 2, the 10-ring pore molecular sieve having a T1/T2 ratio≥20:1 wherein T1 is an element independently selected from Si and Ge or a combination thereof, and T2 is an element independently selected from Al, B and Ga or a combination thereof, the 10-ring pore molecular sieve further having a counterion selected from $NH_4^+$, $Li^+$, $Na^+$, $K^+$ and $Ca^{++}$ or a combination thereof, and contacting the hydrocarbon mixture with the 10-ring pore molecular sieve at a temperature of −20° C. to 60° C. for a time and under conditions to obtain a sieved hydrocarbon mixture comprising the eight-membered monocyclic unsaturated hydrocarbon at a separation concentration $C_s > C_i$, wherein the 10-ring pore molecular sieve has a framework type selected from group consisting of MEL, TUN, IMF, MFI, OBW, MFS and TER, and wherein, the sieved hydrocarbon mixture comprises the eight-membered monocyclic unsaturated hydrocarbon at a separation concentration Cs≥99.3% wt.

2. The sieved hydrocarbon mixture of claim 1, wherein the eight-membered monocyclic unsaturated hydrocarbon is selected from

1

2

3

4

5

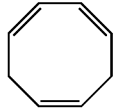
6

-continued

7

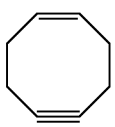
8

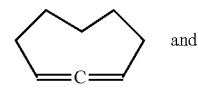
9 and

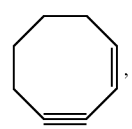
10

, or a combination thereof.

3. The sieved hydrocarbon mixture of claim 1, wherein the eight-membered monocyclic unsaturated hydrocarbon is

1

.

4. The hydrocarbon mixture of claim 1, wherein in the 10-ring pore molecular sieve is a 10-ring pore intermediate molecular sieve wherein the minimum crystallographic free diameter is equal to or greater than 4.5 Å to less than 5 Å and the ratio of the maximum crystallographic free diameter to the minimum crystallographic free diameter is between 1.1 and 1.25.

5. The hydrocarbon mixture of claim 1, wherein in the 10-ring pore molecular sieve is a 10-ring pore wide molecular sieve wherein the minimum crystallographic free diameter is equal to or greater than 5.0 Å to less than 6 Å and the ratio of the maximum crystallographic free diameter to the minimum crystallographic free diameter is between 1.0 and 1.1.

6. The hydrocarbon mixture of claim 1, wherein in the 10-ring pore molecular sieve, the sieving channel is interconnected to one or more sieving channels and/or venting channels to form a 2D channels network.

7. The hydrocarbon mixture of claim 1, wherein in the 10-ring pore molecular sieve, the sieving channel is interconnected to one or more sieving channels and/or venting channels to form a 3D channels network.

8. The hydrocarbon mixture of claim 1, wherein the 10-ring pore molecular sieve has a framework type selected from the group consisting of MEL, TUN, IMF, MFI, OBW, and TER.

9. The hydrocarbon mixture of claim 1, wherein the 10-ring pore molecular sieve is selected from the group consisting of ZSM-5, ZSM-11, IM-5, ZSM-57, OSB-2, Terranovaite, and TNU-9.

10. A hydrocarbon mixture comprising an eight-membered monocyclic unsaturated hydrocarbon and additional nonlinear unsaturated $C_8H_{2m}$ hydrocarbons with $4 \leq m \leq 8$, the eight-membered monocyclic unsaturated hydrocarbon comprised in the hydrocarbon mixture at a concentration of at least 99.5% wt.

11. The hydrocarbon mixture of claim 10, wherein the eight-membered monocyclic unsaturated hydrocarbon comprised in the hydrocarbon mixture at a concentration of at least 99.7% wt.

12. The hydrocarbon mixture of claim 11, wherein the eight-membered monocyclic unsaturated hydrocarbon is selected from the group consisting of

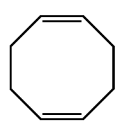
1

2

3

4

5

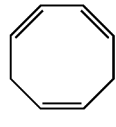
6

7

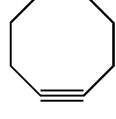
8

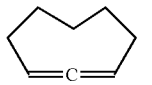 and
9

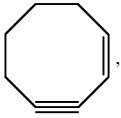,
10 or a combination thereof.

13. The hydrocarbon mixture of claim 11, wherein the eight-membered monocyclic unsaturated hydrocarbon is

.
1

14. The hydrocarbon mixture of claim 11, wherein the eight-membered monocyclic unsaturated hydrocarbon is

.
2

15. The hydrocarbon mixture of claim 10, wherein the eight-membered monocyclic unsaturated hydrocarbon comprised in the hydrocarbon mixture at a concentration of at least 99.8% wt.

16. The hydrocarbon mixture of claim 15, wherein the eight-membered monocyclic unsaturated hydrocarbon is selected from the group consisting of

1

2

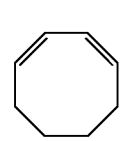
3

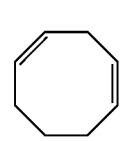
4

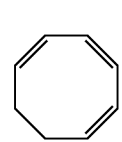
5

6

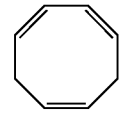
7

 8

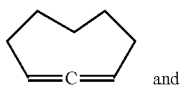 and

, or a combination thereof.

17. The hydrocarbon mixture of claim 15, wherein the eight-membered monocyclic unsaturated hydrocarbon is

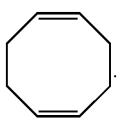 1

18. The hydrocarbon mixture of claim 15, wherein the eight-membered monocyclic unsaturated hydrocarbon is

 2

19. The hydrocarbon mixture of claim 10, wherein the eight-membered monocyclic unsaturated hydrocarbon comprised in the hydrocarbon mixture at a concentration of at least 99.9% wt.

20. The hydrocarbon mixture of claim 19, wherein the eight-membered monocyclic unsaturated hydrocarbon is selected from the group consisting of

 1

 2

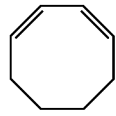 3

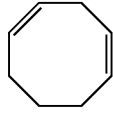 4

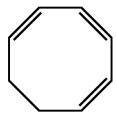 5

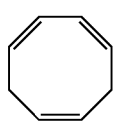 6

 7

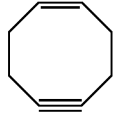 8

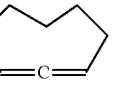 9 and

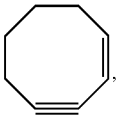 10

, or a combination thereof.

21. The hydrocarbon mixture of claim 19, wherein the eight-membered monocyclic unsaturated hydrocarbon is

 1

22. The hydrocarbon mixture of claim 19, wherein the eight-membered monocyclic unsaturated hydrocarbon is

 2

23. The hydrocarbon mixture of claim 10, wherein the eight-membered monocyclic unsaturated hydrocarbon comprised in the hydrocarbon mixture at a concentration of at least 99.99% wt.

24. The hydrocarbon mixture of claim 23, wherein the eight-membered monocyclic unsaturated hydrocarbon is selected from the group consisting of

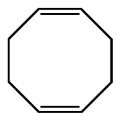

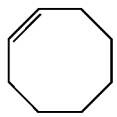

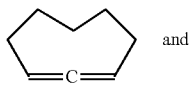
and

, or a combination thereof.

25. The hydrocarbon mixture of claim 23, wherein the eight-membered monocyclic unsaturated hydrocarbon is

.

26. The hydrocarbon mixture of claim 23, wherein the eight-membered monocyclic unsaturated hydrocarbon is

.

27. The hydrocarbon mixture of claim 10, wherein the additional nonlinear unsaturated $C_8H_{2m}$ hydrocarbons with $4 \leq m \leq 8$ comprise at least one compound having structure of Formula (I)

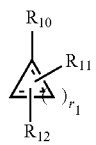

Formula (I)

wherein

------ represents a single bond, or a double bond;

r1 represents 1 to 4;

R10, R11 and R12 are independently selected from H, C1 to C5 linear, branched or cyclic alkyl, alkenyl, or an alkynyl groups, wherein the R11 and R12 are on a same carbon or a different carbon of a ring, and wherein R10, R11 and R12 together contain (6-r1) carbon.

28. The hydrocarbon mixture of claim 10, wherein the additional nonlinear unsaturated $C_8H_{2m}$ hydrocarbons with $4 \leq m \leq 8$, comprise 4-vinyl-1-cyclohexene.

29. A hydrocarbon mixture comprising an eight-membered monocyclic unsaturated hydrocarbon and additional nonlinear unsaturated $C_8H_{2m}$ hydrocarbons with $4 \leq m \leq 8$, the eight-membered monocyclic unsaturated hydrocarbon comprised in the hydrocarbon mixture at a concentration of at least 99.3% wt, wherein the eight-membered monocyclic unsaturated hydrocarbon is selected from the group consisting of

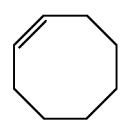

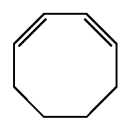

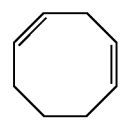

-continued

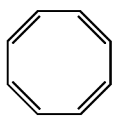

 and

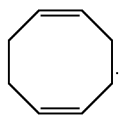

or a combination thereof.

30. The hydrocarbon mixture of claim 29, wherein the eight-membered monocyclic unsaturated hydrocarbon is

31. The hydrocarbon mixture of claim 29, wherein the eight-membered monocyclic unsaturated hydrocarbon is

32. A system to provide a polymer starting from a hydrocarbon mixture comprising an eight-membered monocyclic unsaturated hydrocarbon and additional nonlinear unsaturated $C_8H_{2m}$ hydrocarbons with $4 \leq m \leq 8$, the system comprising
  a 10-ring pore molecular sieve having a sieving channel with a 10-ring sieving aperture with a minimum crystallographic free diameter greater than 3 Å and a ratio of the maximum crystallographic free diameter to the minimum crystallographic free diameter between 1 and 2,
  the 10-ring pore molecular sieve having a T1/T2 ratio≥20:1 wherein T1 is an element independently selected from Si, and Ge or a combination thereof, and T2 is an element independently selected from Al, B, and Ga or a combination thereof,
  the 10-ring pore molecular sieve further having a counterion selected from $NH_4^+$, $Li^+$, $Na^+$, $K^+$ and $Ca^{++}$ or a combination thereof, and
  a polymerization catalyst, and
  a hydrocarbon mixture comprising an eight-membered monocyclic unsaturated hydrocarbon monomer and additional nonlinear unsaturated $C_8H_{2m}$ hydrocarbons with $4 \leq m \leq 8$,
to provide a polymer comprising the eight-membered monocyclic unsaturated hydrocarbon monomer
  wherein the 10-ring pore molecular sieve has a framework type selected from group consisting of MEL, TUN, IMF, MFI, OBW, MFS and TER.

* * * * *